United States Patent
Mahmoud et al.

(10) Patent No.: US 11,179,438 B1
(45) Date of Patent: Nov. 23, 2021

(54) CHICKEN CATHELICIDINS AS A CANCER THERAPY

(71) Applicant: King Abdulaziz University, Jeddah (SA)

(72) Inventors: Maged M. Mahmoud, Jeddah (SA); Haitham A. Yacoub, Giza (EG); Ahmed M. Al-Hejin, Jeddah (SA); Turki Abujaml, Jeddah (SA); Fadwa Aljoud, Jeddah (SA); Modhi Alenezi, Jeddah (SA); Abdulwahab Noorwali, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 17/210,726

(22) Filed: Mar. 24, 2021

(51) Int. Cl.
*A61K 38/17* (2006.01)
*A61P 35/00* (2006.01)

(52) U.S. Cl.
CPC .......... *A61K 38/1729* (2013.01); *A61P 35/00* (2018.01)

(58) Field of Classification Search
CPC .................................................. A61K 38/1729
See application file for complete search history.

(56) References Cited

U.S. PATENT DOCUMENTS

| | | | |
|---|---|---|---|
| 2011/0143999 A1* | 6/2011 | Zhang | C07K 14/465 514/2.4 |
| 2014/0235544 A1 | 8/2014 | Hillman | |
| 2015/0202250 A1 | 7/2015 | Sekaran et al. | |

OTHER PUBLICATIONS

Xing et al. "Recombinant expression and biological characterization of the antimicrobial peptide fowlicidin-2 in Pichia pastoris", Experimental and Therapeutic Medicine, 2016, pp. 2324-2330 (Year: 2016).*
To et al. "Reversal of ABCG2-mediated multidrug resistance by human cathelicidin and its analogs in cancer cells", Peptides, 2013, pp. 13-21 (Year: 2013).*
Veldhuizen et al. "Chicken Cathelicidins Display Antimicrobial Activity against Multiresistant Bacterial without Inducing Strong Resistance", PLOS One, 2013, pp. 1-6 (Year: 2013).*
Chen et al., "Roles and Mechanisms of Human Cathelicidin LL-37 in Cancer", Cell Physiol Biochem 2018; 47:1060-1073.
Kosciuczuk et al., "Cathelicidins: family of antimicrobial peptides. A review", Mol Biol Rep (2012) 39:10957-10970.
Scheenstra et al., "Cathelicidins Modulate TLR-Activation and Inflammation", (2020) Front. Immunol. 11:1137.
Wang et al., "Avian host defense cathelicidins: structure, expression, biological functions, and potential therapeutic applications", (2020) Poultry Science 99:6434-6445.

* cited by examiner

Primary Examiner — Lianko G Garyu
(74) Attorney, Agent, or Firm — W&C IP

(57) ABSTRACT

Methods of treating cancer, such as breast cancer or colorectal cancer, in a subject are provided. The methods include administering to the subject a therapeutically effective amount of a chicken cathelicidin, such as cathelicidin-1, cathelicidin-2, or cathelicidin-3. Methods of inhibiting the growth of cancer cells are also provided.

10 Claims, 12 Drawing Sheets

Specification includes a Sequence Listing.

SEQUENCE LISTING

```
<160> NUMBER OF SEQ ID NOS: 19

<210> SEQ ID NO 1
<211> LENGTH: 26
<212> TYPE: PRT
<213> ORGANISM: Gallus gallus

<400> SEQUENCE: 1

Arg Val Lys Arg Val Trp Pro Leu Val Ile Arg Thr Val Ile Ala Gly
1               5                   10                  15

Tyr Asn Leu Tyr Arg Ala Ile Lys Lys Lys
            20                  25

<210> SEQ ID NO 2
<211> LENGTH: 26
```

```
-continued

<212> TYPE: PRT
<213> ORGANISM: Gallus gallus

<400> SEQUENCE: 2

Arg Phe Gly Arg Phe Leu Arg Lys Ile Arg Arg Phe Arg Pro Lys Val
1               5                   10                  15

Thr Ile Thr Ile Gln Gly Ser Ala Arg Phe
            20                  25

<210> SEQ ID NO 3
<211> LENGTH: 29
<212> TYPE: PRT
<213> ORGANISM: Gallus gallus

<400> SEQUENCE: 3

Arg Val Lys Arg Phe Trp Pro Leu Val Pro Val Ala Ile Asn Thr Val
1               5                   10                  15

Ala Ala Gly Ile Asn Leu Tyr Lys Ala Ile Arg Arg Lys
            20                  25

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
accccaagag tggagttgtg                                            20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
ggaaggcatt ttctgatcca                                            20

<210> SEQ ID NO 6
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 6
gtgctgcgaa gtggaaacc                                             19

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 7
atccaggtgg cgacgatct                                             19

<210> SEQ ID NO 8
<211> LENGTH: 22
<212> TYPE: DNA
<213> ORGANISM: Artificial Sequence
<220> FEATURE:
```

-continued

<223> OTHER INFORMATION: Synthetic oligonucleotide

<400> SEQUENCE: 8 caaactttt cagaggggat cg                                      22

<210> SEQ ID NO 9
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 9
gcatactgtt tcagcatggc ac                                     22

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
tgagccacgg agaagagaat                                        20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
tttgcttact ccacggttcc                                        20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
gtattgggcg cctggtcacc                                        20

<210> SEQ ID NO 13
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 13
cgctcctgga agatggtgat gg                                     22

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
tcgaccctac atggccttac                                        20

```
-continued

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
gctgggtctt ctcctgttct                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
tgagcccatg aagcagacat                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
tggcatttgg tcccatctct                                               20

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonueotide

<400> SEQUENCE: 18
tgtttgtgat gggtgtgaac c                                             21

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
catgagccct tccacaatgc                                               20
```

CHICKEN CATHELICIDINS AS A CANCER THERAPY

FIELD OF THE INVENTION

The invention is generally related to chicken cathelicidins useful for the treatment of cancer.

BACKGROUND OF THE INVENTION

There is an in-built immune and defense system in every organism that protects its body from disease-causing microbes or pathogens. The immune system generates small microbe-killing molecules in order to prevent and counter the pathogen attack; such molecules are known as antimicrobial peptides. Multifunctional properties of AMPs have been lately recognized; they are known to perform multiple roles of immune regulation, wound healing, angiogenesis, and anticancer functions. They show different anticancer properties according to cancer types (Kuroda et al., 2015). Since the antimicrobial peptides are positively charged particles, they easily undergo reaction with the microbial cell surface that is negatively charged (Parvy et al., 2019). As a result, the cell surfaces are disrupted. In healthy animals, the negative charge is not visible to the AMPs due to absence of such negatively charged particles on the cell surface. The growth of cancer cells placed in a dish was found to be attacked by the AMPs according to various studies but AMPs attack on cancer cells within a living body have not been established yet (Parvy et al., 2019).

One type of peptide essential for the natural immune system is Cathelicidins which are one of the two types of Host Defense Peptides (HDP). These peptides are characterized with multiple antimicrobial activities for prevention of attack by Gram-negative bacteria, Gram-positive bacteria, fungi and parasites. The in vitro examinations revealed that cathelicidins-1, -2 and -3 depicted potent broad spectrum antibacterial activities; on the other hand, only some of the bacteria were subjected to CATH-B1. Considering other peptides, gene duplication leads to the formation of mature peptides CATH-1 and CATH-3 having about 70% similar sequence (Goitsuka et al., 2007; Xiao et al., 2006; Achanta et al., 2012). However, only their antibacterial properties have been extensively studied in the majority of research (Cuperus et al., 2013, 2016; Lee et al., 2012, 2016; Zasloff, 2019). Several studies have investigated the antimicrobial and immunomodulatory potentialities of chicken cathelicidin-2 through activating toll like receptor (2) and neutralization of LPS (Van Dijk et al., 2009, 2016; Coorens et al., 2015, 2017, Peng et al., 2020a,b).

The significance and processes of LL-37 (human cathelicidin) in case of human cancer was only investigated at molecular and cellular levels. It was found that LL-37 may act as a pro-tumorigenic agent or as an anti-cancer agent. LL-37 effects at the molecular level in various cellular settings have not been comprehended completely; but its function as a ligand for different membrane receptors has been recognized which indicates the tissue-specific activity of LL-37 in various types of cancers (Chen et al., 2018). Various combinations of processes like aberrant cell cycle regulation, decline in rate of apoptosis and increased stimulation of growth factor pathway affect the malignant transformation and onset and progression of the tumor (Blagoskonny and Pardee, 2001). The progression of the cell cycle is controlled through the coordination of serine/threonine kinases namely the Cyclin-dependent kinases (CDKs). When the CDK enzyme complex binds to the appropriate cyclin, it is activated. When the phosphoryl group is added to this CDK-cyclin complex at specific activating residues, then planned activation and breakdown of CDK complexes is essential for controlling cell cycle progression (Nurse, 2002; Gadek et al., 2004). The CDK activity is greater in transformed cells than in normal ones; hence, the former show quicker cell proliferation. This implies the therapeutic significance of inhibiting CDK/cyclin complexes in protection from cancer. Cells are blocked during the G phase of cell cycle by compounds inhibiting CDK4/6 activity, while cell arrest during G/S and G/M phases of cell cycle is caused by compounds inhibiting CDK1/2 activity (Nurse, 2002).

Moreover, apoptosis may be stimulated in cancer cells by a few inhibitors of CDK2 activity. With respect to structure, CDK inhibitors (CDKIs) are associated with adenosine-5'-triphosphate (ATP) (Gadek et al., 2004).

Improved agents for the treatment of cancer are needed.

SUMMARY

Described herein are chicken cathelicidin peptides useful for the treatment of cancer. An aspect of the disclosure provides a method of treating cancer in a subject in need thereof, comprising administering to the subject a therapeutically effective amount of a chicken cathelicidin or an active analog thereof. In some embodiments, the cathelicidin is cathelicidin-1. In some embodiments, the cathelicidin is cathelicidin-2. In some embodiments, the cathelicidin is cathelicidin-3. In some embodiments, the cancer is breast cancer. In some embodiments, the cancer is colorectal cancer. In some embodiments, the chicken cathelicidin is administered at a dose of 5 to 45 mg/kg. In some embodiments, the subject is human.

Another aspect of the disclosure provides a method of inhibiting the growth of cancer cells, comprising contacting the cancer cells with an effective amount of a chicken cathelicidin or an active analog thereof.

DETAILED DESCRIPTION

Figure 1A:
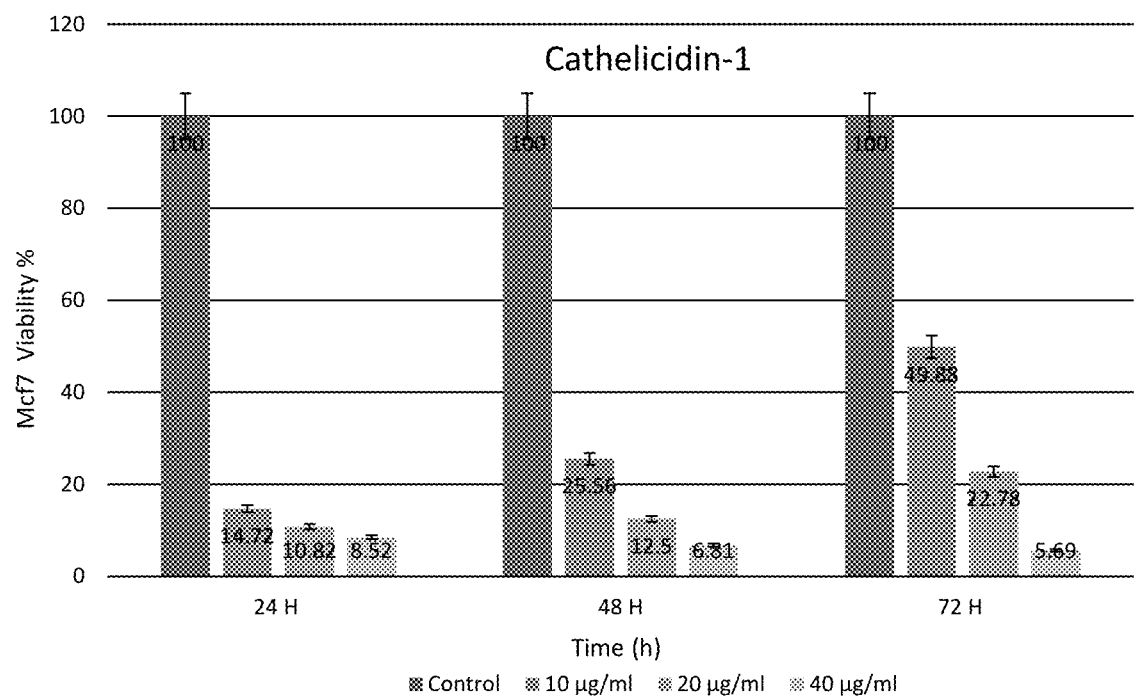
FIGS. 1A-F. Anticancer activity of chicken cathelicidin peptides (A) cathelicidin-1, (B) cathelicidin-2, and (C) cathelicidin-3 against breast cancer cells (MCF-7) and of (D) cathelicidin-1, (E) cathelicidin-2, and (F) cathelicidin-3 against colon cancer cells (HCT116). Untreated cells were used as a control. Data presented as mean (±SD) of three independent repeats in triplicate.
Figure 1B:
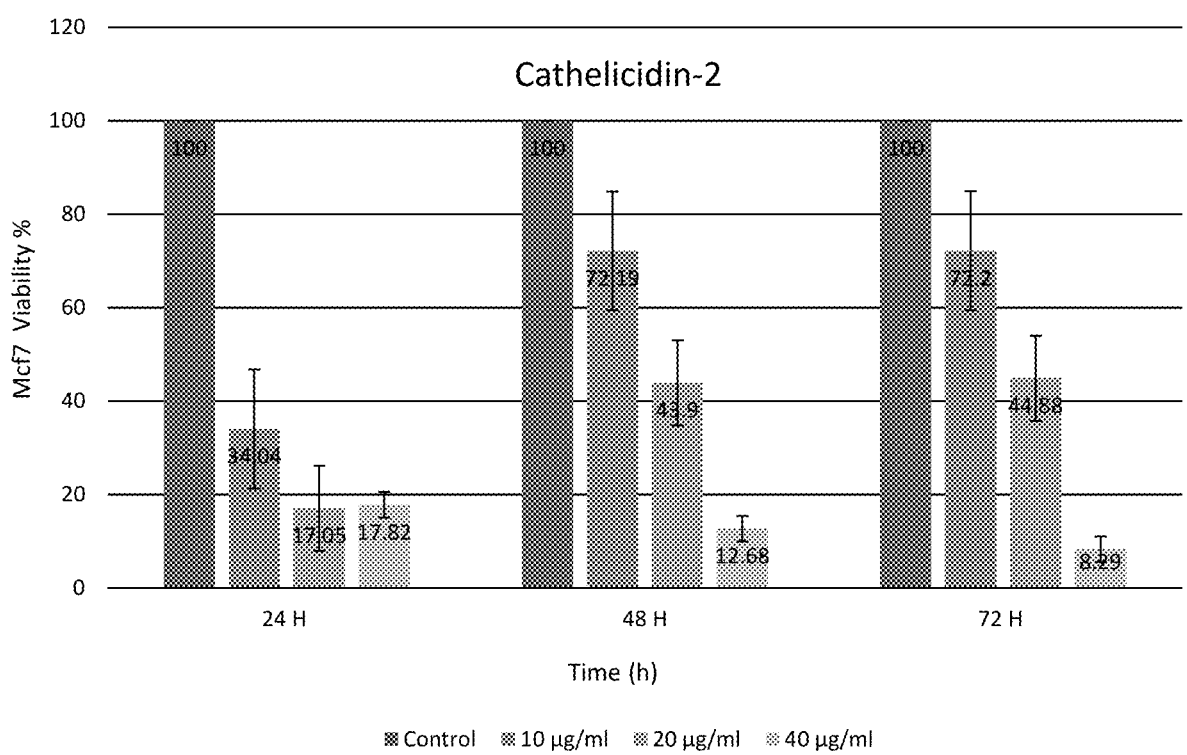
Figure 1C:
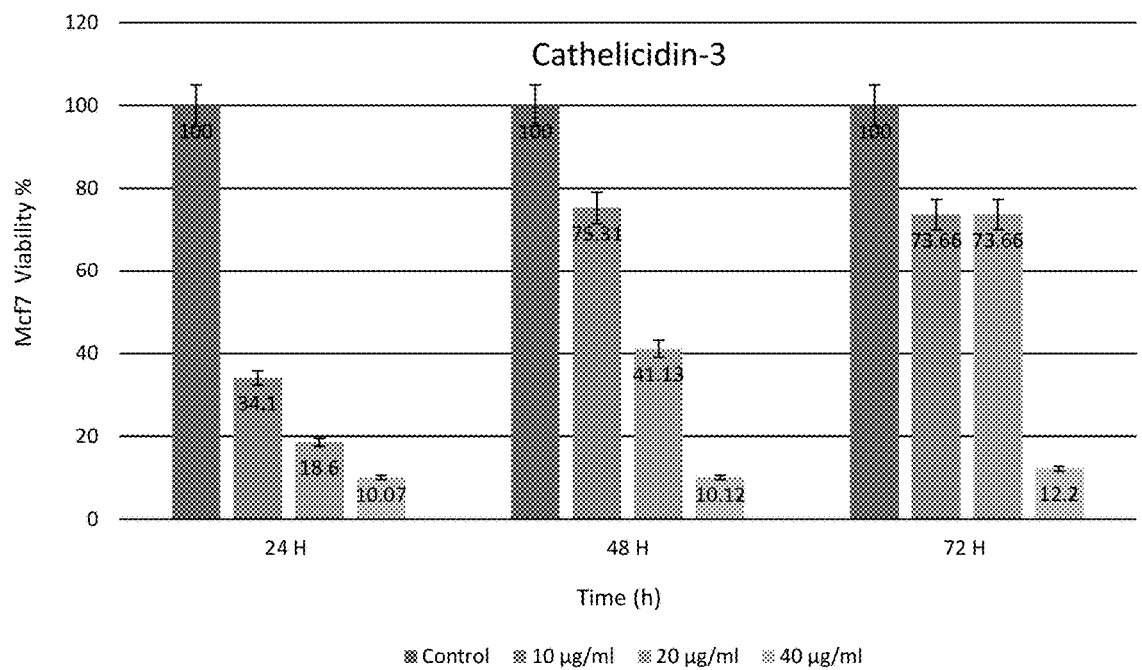
Figure 1D:
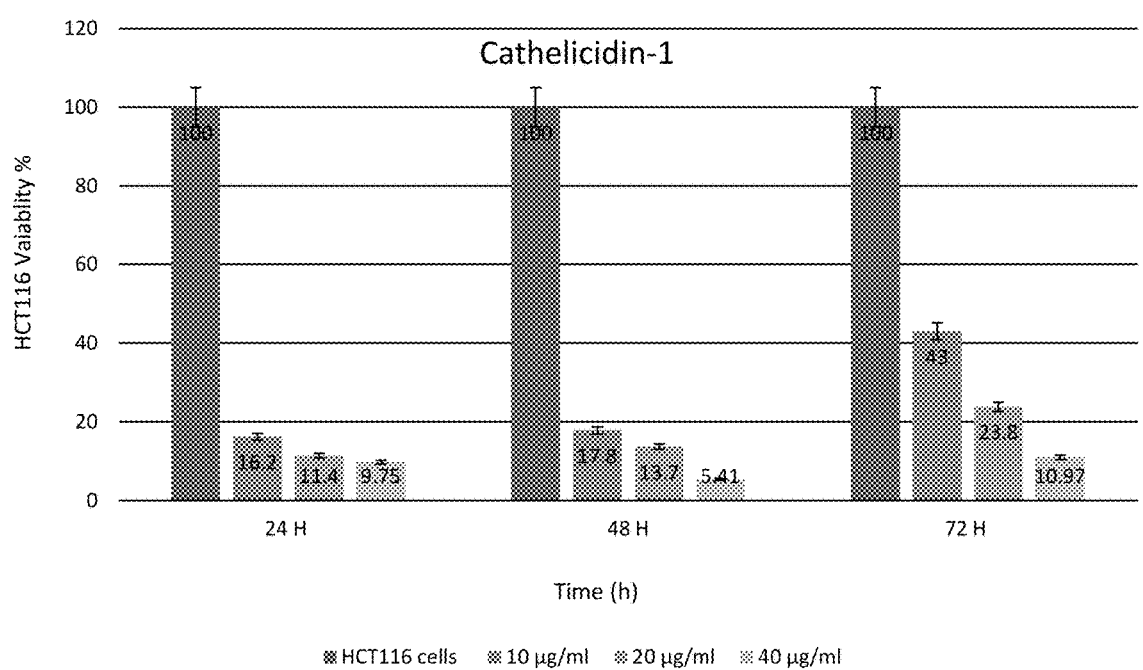
Figure 1E:
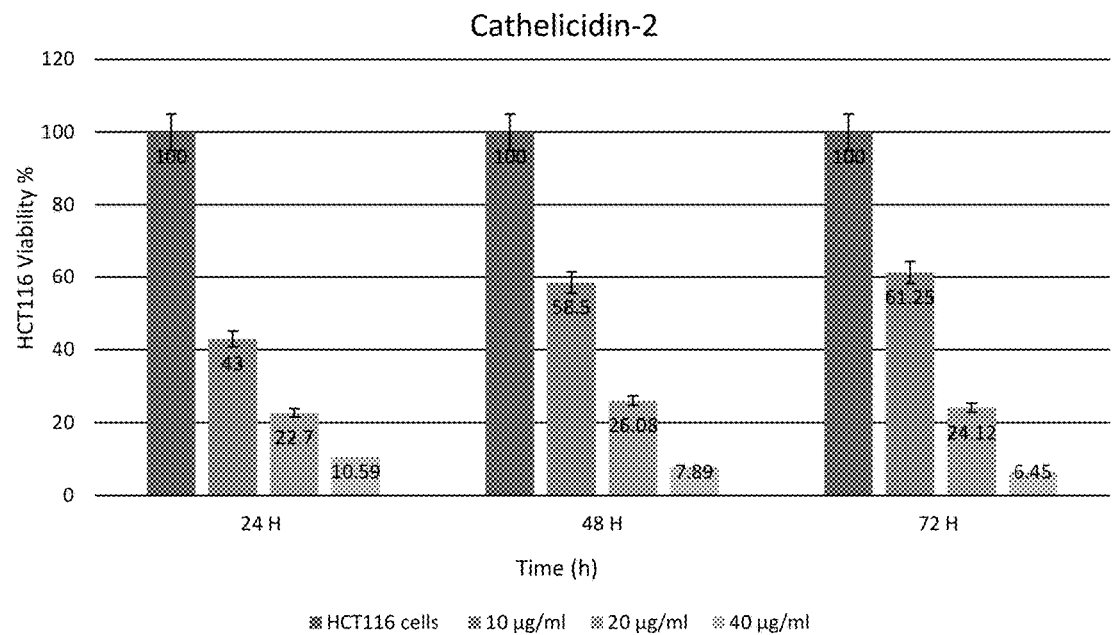
Figure 1F:
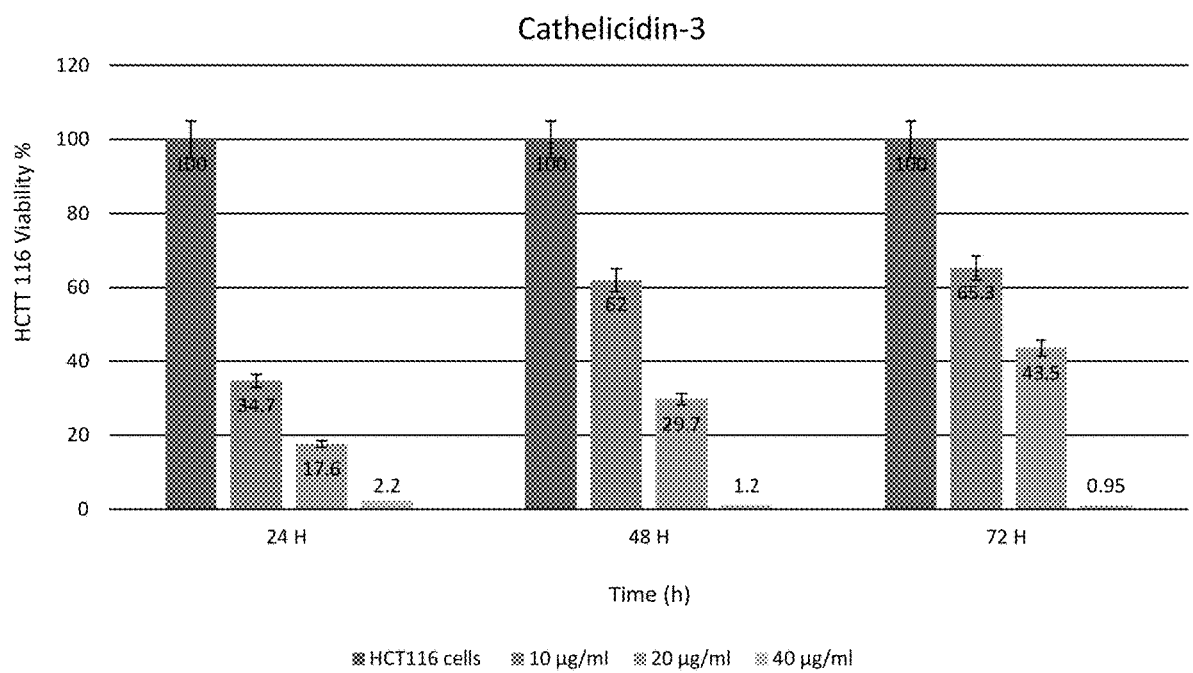

Embodiments of the disclosure provide methods of treating cancer in a subject by administering a therapeutically effective amount of a chicken cathelicidin or an active analog thereof.

Cathelicidins are Host Defence Peptides (HDP) that play an important role in the innate immune system. They exhibit broad range antimicrobial activity against both Gram-negative and Gram-positive bacteria, as well as against fungi and parasites. In chicken, four cathelicidins (CATH-1-3 and CATH-B1) have been described. The first three cathelicidins have shown potent broad spectrum antibacterial activity in vitro, while CATH-B1 has only been tested against a limited number of bacterial strains. The mature forms of CATH-1 and CATH-3 share a high sequence homology (>70%), and are thought to be the result of gene duplication. However, no apparent homology is present between CATH-1/-3 with CATH-2 and CATH-B1. Structurally, CATH-1 and CATH-3 are also very similar having a mainly linear alpha helical shape, while CATH-2 contains a proline-induced hinge region in the middle of the peptide. This provides a kink in the three-dimensional structure of the peptide, which has been shown to be important for both antibacterial and immunomodulatory roles. CATH-1 and CATH-2 are mainly produced in bone marrow with lower expression levels in several other tissues. CATH-2 is present in heterophils and is released from these cells upon degranulation of these cells. Contrary to this localization in immune cells, CATH-B1 is exclusively produced in the epithelial cells surrounding the M-cells in the bursa of Fabricius, suggesting that this peptide has a local role in forming a defense layer to protect the bursa from infection, although low levels of CATH-B1 RNA were also found in other tissues.

Any chicken cathelicidin or an active analog/fragment thereof may be administered to a subject for the treatment of cancer.

A "fragment" of a cathelicidin polypeptide refers to any portion of the polypeptide smaller than the full-length polypeptide or protein expression product. Fragments are, in one aspect, deletion analogs of the full-length polypeptide wherein one or more amino acid residues have been removed from the amino terminus and/or the carboxy terminus of the full-length polypeptide. Accordingly, "fragments" are a subset of deletion analogs described below.

An "analogue," "analog" or "derivative" is a compound substantially similar in structure and having the same biological activity, albeit in certain instances to a differing degree, to a naturally-occurring molecule. For example, a polypeptide analog refers to a polypeptide sharing substantially similar structure and having the same biological activity as a reference polypeptide. Analogs differ in the composition of their amino acid sequences compared to the naturally-occurring polypeptide from which the analog is derived, based on one or more mutations involving (i) deletion of one or more amino acid residues at one or more termini of the polypeptide and/or one or more internal regions of the naturally-occurring polypeptide sequence, (ii) insertion or addition of one or more amino acids at one or more termini (typically an "addition" analog) of the polypeptide and/or one or more internal regions (typically an "insertion" analog) of the naturally-occurring polypeptide sequence or (iii) substitution of one or more amino acids for other amino acids in the naturally-occurring polypeptide sequence.

In some embodiments, an isolated cathelicidin peptide has between 15 and 50 amino acids, where the peptide exhibits antitumoral or anticancer activity, and where the peptide contains a sequence comprising at least 15, 16, 17, 18, 19, 20, 21, 22, 23, 24, 25, 26, 27, 28, 29, 30, 35, or 40 contiguous amino acids from any of the cathelicidin sequences disclosed herein. In some embodiments, the peptide has a length of 15-40 amino acids, e.g. about 20-30 amino acids. In some embodiments, the peptide comprises a sequence as set forth in SEQ ID NO: 1, SEQ ID NO: 2, or SEQ ID NO: 3 which corresponds to cathelicidin-1, cathelicidin-2, and cathelicidin-3, respectively.

By an "isolated peptide" is meant a presently disclosed peptide that has been separated from components that naturally accompany it. Typically, the peptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a presently disclosed peptide. An isolated peptide may be obtained, for example, by extraction from a natural source, by expression of a recombinant nucleic acid encoding such a peptide; or by chemically synthesizing the protein. Purity can be measured by any appropriate method, for example, column chromatography, polyacrylamide gel electrophoresis, or by HPLC analysis.

In some embodiments, the peptide contains at least one amino acid substitution relative to the naturally occurring cathelicidin sequence. The peptides of the disclosure also may comprise peptide sequences that exhibit 70% or more sequence identity, e.g. 70%, 75%, 80%, 85%, 90%, 91%, 92%, 93%, 94%, 95%, 96%, 97%, 98%, 99% or more sequence identity, e.g. as determined by BLAST or FASTA algorithms, with at least 7, 10, 15, 20, 25, 30, 35, or 40 contiguous amino acids from any of the sequences disclosed herein.

In some embodiments, the peptide contains a conserved amino acid substitution. Conserved amino acid substitutions involve replacing one or more amino acids in a peptide sequence with amino acids of similar charge, size, and/or hydrophobicity characteristics. Amino acids may be substituted with an amino acid within the same group according to the following categories: acid, basic, polar neutral, and non-polar neutral. For example a conservative mutation would include substitution of one small, neutral, non-polar amino acid such as alanine, glycine, isoleucine, leucine, proline, and valine for another. Similarly, mutation of a glutamic acid to an aspartic acid, or vice versa would also be considered a conservative mutation. Exchange of phenylalanine, tyrosine, and tryptophan for each other would be considered a conservative mutation. When only conserved substitutions are made, the resulting peptide retains the functionality of the unsubstituted peptide. In some embodiments, the peptide includes nonconserved substitutions, e.g. to enhance the efficacy of the peptide.

In some embodiments, the peptide is conjugated or linked to a macromolecule or drug carrier, for example, lipid-fatty acid conjugates, polyethylene glycol, or carbohydrates. Ex vivo conjugation of the peptides to a macromolecule such as human serum albumin (HSA) produces a highly soluble conjugate that can be purified and administered in tightly controlled dosage. The cloaked conjugate is biologically active as the conjugate, i.e. it does not act as a prodrug that releases the peptide moiety from the conjugate and cleavage of the conjugate is not required for biological activity. In some embodiments, the peptide and the macromolecule are linked in an approximately 1:1 ratio, to avoid "haptenization" of the biologically active moiety and generation of an immune response to the conjugate. In some embodiments, more than one molecule of peptide is linked to the macromolecule, which may be achieved via a "multivalent" linker that is attached to a single point of the macromolecule. For example, a linker can be appended to C34 of HSA that permits attachment of a plurality of peptides to the linker. Multivalent linkers are known in the art and can contain, for example, a thiophilic group for reaction with C34 of HSA, and multiple nucleophilic (such as NH or OH) or electrophilic (such as activated ester) groups that permit attachment of a plurality of peptides to the linker.

Activated linkers that are particularly suited for linkage to thiols include unsaturated cyclic imides such as maleimides, α-halo esters, such as α-iodo- and α-bromo acetates, and vinyl pyridine derivative. Such linkers can be added to the peptides during synthesis and can be added at any point in the sequence although the N and/or C terminus advantageously is used. Suitable activated linkers are commercially available from, for example, Pierce Chemical (Rockford, Ill.). Methods for preparing suitable activated compounds for linking to HSA are known in art. See for example, U.S. Pat. No. 5,612,034, which is incorporated herein in its entirety.

Another blood component that is suitable for linkage to the anti-viral compounds is an immunoglobulin ("Ig") molecule. An Ig refers to any suitable immunoglobulin or immunogolobulin derivative known in the art, and includes, for example, whole IgG, IgM, Fab fragments, F(ab')2 fragments, and single chain Fv fragments.

Other blood components suitable for use in the present disclosure include transferrin, ferritin, steroid binding proteins, thyroxin binding protein, and α-2-macroglobulin.

In some embodiments, the peptides may be synthesized with additional chemical groups present at their amino and/or carboxy termini, such that, for example, the stability, bioavailability, and/or inhibitory activity of the peptides is enhanced. For example, hydrophobic groups such as carbobenzoxyl, dansyl, or t-butyloxycarbonyl groups, may be added to a peptide's amino terminus. Likewise, an acetyl group or a 9-fluorenylmethoxy-carbonyl group may be placed at a peptide's amino terminus. Additionally, a hydrophobic group, t-butyloxycarbonyl, or an amido group may be added to a peptide's carboxy terminus. Further, non-naturally occurring amino acids can be used to improve a peptide's stability, bioavailability, or binding/inhibitory characteristics. For example, methionine can be replaced with norleucine. Other non-naturally occurring amino acid residues are well known.

Further embodiments provide a nanoparticle or microparticle comprising peptide as described herein. The peptide may be loaded onto or into, or otherwise associated with the particle. In particular embodiments, the microparticle or nanoparticle comprises a biodegradable polymer or blends of polymers selected from the group consisting of poly (lactic-co-glycolic acid) (PLGA), poly(beta-amino ester) (PBAE), polycaprolactone (PCL), polyglycolic acid (PGA), polylactic acid (PLA), poly(acrylic acid) (PAA), poly-3-hydroxybutyrate (P3HB) and poly(hydroxybutyrate-co-hydroxyvalerate). In other embodiments, nondegradable polymers that are used in the art, such as polystyrene, are blended with a degradable polymer or polymers from above to create a copolymer system. Accordingly, in some embodiments, a nondegradable polymer is blended with the biodegradable polymer.

Further embodiments provide nanoantibiotics containing membrane-active human cathelicidin LL-37 and synthetic ceragenins attached to the surface of magnetic nanoparticles.

The peptides of the disclosure may be synthesized or prepared by techniques well known in the art. Peptide synthesizers are commercially available from, for example, Applied Biosystems or Milligen/Biosearch. See also, for example, Creighton, 1983, Proteins: Structures and Molecular Principles, W. H. Freeman and Co., N.Y. Short peptides, for example, can be synthesized on a solid support or in solution. Longer peptides, or fusions of longer peptides with carrier proteins such as human serum albumin, may be made using recombinant DNA techniques. Nucleotide sequences encoding the desired peptides or fusion proteins containing the peptides may be synthesized, and/or cloned, and expressed according to techniques well known to those of ordinary skill in the art. See, for example, Sambrook, et al., 1989, Molecular Cloning, A Laboratory Manual, Vols. 1-3, Cold Spring Harbor Press, N.Y.

The peptides also may be synthesized such that one or more of the bonds linking the amino acid residues of the peptides are non-peptide bonds. Alternative non-peptide bonds may be formed by reactions well known to those in the art, and may include, but are not limited to imino, ester, hydrazide, semicarbazide, and azo bonds.

Further embodiments provide a pharmaceutical composition comprising a peptide or composition as described herein and a pharmaceutically acceptable diluent, adjuvant and/or excipient.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Suitable pharmaceutically acceptable carriers include but are not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. Other suitable excipients include, for example an inert diluent such as lactose; granulating and disintegrating agents such as cornstarch; binding agents such as starch; and lubricating agents such as magnesium stearate.

The compositions may be provided in the form of tablets, coated tablets, dragees, hard or soft gelatin capsules, solutions, emulsions or suspensions.

The compositions of the present disclosure may also contain other components such as, but not limited to, anti-oxidants, additives, adjuvants, buffers, tonicity agents, bio-adhesive polymers, and preservatives. It should be appreciated that the compositions of the present disclosure may be buffered by any common buffer system such as phosphate, borate, acetate, citrate, carbonate and borate-polyol complexes, with the pH and osmolality adjusted in accordance with well-known techniques to proper physiological values.

An additive such as a sugar, a glycerol, and other sugar alcohols, can be included in the compositions of the present disclosure. Pharmaceutical additives can be added to increase the efficacy or potency of other ingredients in the composition. For example, a pharmaceutical additive can be added to a composition of the present disclosure to improve the stability of the bioactive agent, to adjust the osmolality of the composition, to adjust the viscosity of the composition, or for another reason, such as effecting drug delivery. Non-limiting examples of pharmaceutical additives of the present disclosure include sugars, such as, trehalose, mannose, D-galactose, and lactose.

In an embodiment, if a preservative is desired, the compositions may optionally be preserved with any well-known system such as benzyl alcohol with/without EDTA, benzalkonium chloride, chlorhexidine, Cosmocil® CQ, or Dowicil 200.

Further embodiments provide a method of inhibiting the growth of cancer cells comprising contacting the cells (e.g. in vitro) with an effective amount of a peptide or composition as described herein.

Further embodiments provide a method of treating or preventing cancer in a subject, comprising administering to a patient suffering from (or suspected of suffering from) the cancer a therapeutically effective amount of a peptide or composition as described herein.

Any type of cancer may be treated by the methods disclosed herein including, but not limited to, breast, colorectal, hepatic, lung, pancreatic, skin, intestinal, brain, kidney, blood, stomach, esophageal, prostate, uterine, cervical, and ovarian cancer. In some embodiments, the peptide is not administered with any other anti-cancer active agent.

A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

In some embodiments, the peptide or composition is administered to the subject in a therapeutically effective amount. By a "therapeutically effective amount" is meant a sufficient amount to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000.0 mg per adult per day. In particular, the compositions contain 0.01, 0.05, 0.1, 0.5, 1.0, 2.5, 5.0, 10.0, 15.0, 25.0, 50.0, 100.0, 250.0 and 500.0 mg of the active ingredient for the symptomatic adjustment of the dosage to the subject to be treated. A medicament typically contains from about 0.01 mg to about 500.0 mg of the active ingredient, in particular from 1.0 mg to about 100.0 mg of the active ingredient. An effective amount of the drug is ordinarily supplied at a dosage level from 5 mg/kg to about 45 mg/kg of body weight per day, e.g. 10-40 mg/kg or 20-40 mg/kg.

Any mode of administration may be used including, but not limited to, transdermal, intraperitoneal, intracranial, intracerebroventricular, intracerebral, intravaginal, intrauterine, oral, rectal, ophthalmic (including intravitreal or intracameral), nasal, topical (including buccal and sublingual), parenteral (including subcutaneous, intraperitoneal, intramuscular, intravenous, intradermal, intracranial, intratracheal, and epidural) administration.

The active agent (cathelicidins or analogs thereof) may be combined with pharmaceutically acceptable excipients. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

For injection, the peptides may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Other diluents, adjuvants, and excipients are known in the art.

The peptides may be formulated with a suitable adjuvant in order to enhance the immunological response. Such adjuvants may include, but are not limited to mineral gels such as aluminum hydroxide; surface active substances such as lysolecithin, pluronic polyols, polyanions; other peptides; oil emulsions; and potentially useful human adjuvants such as BCG and *Corynebacterium parvum*.

Further embodiments provide a kit containing some or all of the components, reagents, supplies, and the like to practice a method according to the presently disclosed subject matter. In one embodiment, a kit comprises at least one container (e.g. a vial, tube, or ampoule) comprising an isolated peptide.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example

Summary

This study served as the pioneer in studying the anticancer role of chicken cathelicidin peptides. Chicken cathelicidins were used as anticancer agent against the breast cancer cell line (MCF-7) and human colon cancer cell line (HCT116). An in vivo investigation was also achieved to evaluate the role of chicken cathelicidin in Ehrlich ascites cell (EAC) suppression as a tumor model after subcutaneous implantation in mice. In addition, the mechanism of action of the interaction of cationic peptides with breast cancer cell line MCF-7 was also investigated. It was found during the study that exposure of cell lines to higher concentrations of chicken cathelicidin for 72 h reduced cell lines growth rate by 90%-95%. These peptides demonstrated down-regulation of (cyclin A1 and cyclin D genes) which are essential for G1/S phase transient and S/G2 phase and consequently causes "prometaphase arrest" ultimately leading to death of MCF-7 cells. The study showed two- and three-times higher expression of the caspase-3, and -7 genes respectively in MCF-7 cells treated with chicken peptides (especially cathelicidin-2 and -3) relative to untreated cells which encouraged pro-apoptotic pathway, autophagy, and augmentation of the anti-proliferative activity. Our data showed that chicken cathelicidins enhance release of TNFα, INF-γ and upregulation of granzyme K in treated mice groups, in parallel, the tumor size and volume was reduced in the treated EAC-bearing groups after cathelicidin administration compared to untreated EAC-bearing group. Additionally, animals receiving a high dose of cathelicidin-1 (40 µg/ml) displayed an apical survival rate compared to untreated carcinoma control and animals which received low dose of cathelicidin (10 and 20 µg/ml). Tumors of mice groups treated with chicken cathelicidin displayed high area of necrosis compared to untreated EAC-bearing mice. Histological analysis and immunohistochemical staining revealed that the tumor section in Ehrlich solid tumor exhibited a strong Bcl2 expression in untreated control compared to mice treated with 10 & 20 µg/ml of cathelicidin. Interestingly, low expression of Bcl2 were observed in mice taken 40 µg/ml of CATH-1.

Material and Methods

The experiments were carried out in multiples of three and were repeated at three different times. Negative controls in all experiments for determining the impact of chicken cathelicidins peptides were MCF-7 cells cultivated in their absence.

Peptides

The synthesis of mature peptides of chicken cathelicidins peptides were carried out by (Peptide 2.0, USA) peptide2.com. HPLC was used to purify the three peptides up to 95%, and it was shown in mass spectrometry analysis. Sequences of amino acids of these mature peptides are as shown in Table 1.

TABLE 1

The amino acid sequence of the three chicken cathelicidins peptides

| Peptide name | Amino Acid Sequence | M.W |
|---|---|---|
| Cathelicidin-1 | RVKRVWPLVIRTVIAGYNLYRAIKKK (SEQ ID NO: 1) | 3399.92 |
| Cathelicidin-2 | RFGRFLRKIRRI-RPKVTITIQGSARF (SEQ ID NO: 2) | 3419.16 |
| Cathelicidin-3 | RVKRFWPLVPVAINTVAAGINLYKAIRRK (SEQ ID NO: 3) | 3568.07 |

Cell Culture and Treatment

The breast (MCF-7) and colon cancer (HCT116) cell lines were purchased from the American Type Culture Collection (Manassas, Va., USA) and maintained at 37° C. in a 1:1 mixture of Dulbecco's modified Eagle's medium DMEM high glucose (4.5 g/L) supplemented with 10% FBS in Corning®T75 flasks containing 1.2 g/l sodium bicarbonate (Sigma-Aldrich, St. Louis, Mo., USA), 2.5 mM L-glutamine (Invitrogen Life Technologies), 15 mM HEPES, and 0.5 mM sodium pyruvate supplemented with 400 ng/ml hydrocortisone (Sigma-Aldrich) and 10% fetal bovine serum (PAA Laboratories, Pasching, Austria) in a humidity incubator with 5% CO2 and 95% air. The culture medium was refreshed every 2-3 days for a period of 5-7 days to allow for recovery from cryopreservation and for confluency to be reached. For cell subculturing, the cells were digested with 0.25% trypsin and 0.03% EDTA solution (Invitrogen Life Technologies). Upon reaching 90% confluency, cell numbers were counted. The density of cells was 5 λ103 cells/cm². After that, the MCF-7 cells were seeded into three 96 well plates and treated with three chicken cathelicidins peptides for three period of incubations (24 h-48 h-72 h) (Li et al., 2014).

Cell Viability Assay

To assess the altered cell viability, Cell Counting Kit-8 (CCK-8) assay (Dojindo Laboratories, Kumamoto, Japan) was performed. Briefly, the cells were seeded in 96-well plates at $5 \times 10^3$ cells/well containing 180 µl of medium and cultured for up to 72 h. At the end of each experiment, 5 µl of CCk-8 solution (5 mg/ml) was added into each well, and the cells were incubated for 2 h at 37° C. The optical density value was measured by using BioTek microplate reader (Dynatech Laboratories Inc., Chantilly, Va., USA) at 450 nm. The median inhibition concentration (IC50) values were calculated using the probity model, and the inhibition rate of cell proliferation was calculated as: inhibition rate (%)=1−A450 (test)/A450 (control)×100%. Data were calculated from three independent experiments, each performed in triplicate (Li et al., 2014).

RNA Isolation

Total RNA was isolated from MCF-7 cells after chicken cathelicidins treatment using EZ RNA Clean Up Plus DNase Kit (EZ BioResearch, St Louis, Mo., USA)) following the manufacturer's instructions. RT-PCR was performed by using 1 µg of total RNA samples in the Access RT-PCR System (Bioneer Corporation Co., Ltd, South Korea) under the following conditions: first-strand DNA was synthesized with 12 cycles at 37° C. for 10 sec, 48° C. for 4 min and 60° C. for 30 sec and finally, heat inactivation at 95° C. for 5 mins then denatured at 94° C. for 5 min for the first cycle but for 30 sec for the additional 35 cycles; annealing according to Table 2 for 30 sec and extension at 72° C. for 2 min; and a final extension at 72° C. for 10 min. The PCR products were then subjected to electrophoresis in a 1.2% agarose gel and stained with ethidium bromide.

TABLE 2

List of primers for detection and characterization of cell cycle division genes and caspases executioner genes

| Gene | Forward Primer (5' to 3') | Reverse primer (5' to 3') | Annealing temperature (° C.) | References |
|---|---|---|---|---|
| Cyclin A-1 | ACC CCA AGA GTG GAG TTG TG (SEQ ID NO: 4) | GGA AGG CAT TTT CTG ATC CA (SEQ ID NO: 5) | 53 | Hendriksen et al., 2009 |
| Cyclin D-1 | GTG CTG CGA AGT GGA AAC C (SEQ ID NO: 6) | ATC CAG GTG GCG ACG ATC T (SEQ ID NO: 7) | 57 | Hendriksen et al., 2009 |
| Caspase-3 | CAAACTTTTTCAGAG GGGATCG (SEQ ID NO: 8) | GCATACTGTTTCAGC ATGGCAC (SEQ ID NO: 9) | 55 | Hendriksen et al., 2009 |
| Caspase-7 | TGAGCCACGGAGAA GAGAAT (SEQ ID NO: 10) | TTTGCTTACTCCACGG TTCC (SEQ ID NO: 11) | 53 | Hendriksen et al., 2009 |
| GAPDH | GTA TTG GGC GCC TG G TCACC (SEQ ID NO: 12) | CG C TCC TGG AAG AT G GTG ATG G (SEQ ID NO: 13) | 60 | Harrois et al., 2014 |
| mouse granzyme B | TCGACCCTACATGGC CTTAC (SEQ ID NO: 14) | GCTGGGTCTTCTCCTG TTCT (SEQ ID NO: 15) | 60 | |
| mouse granzyme K | TGAGCCCATGAAGCA GACAT (SEQ ID NO: 16) | TGGCATTTGGTCCCAT CTCT (SEQ ID NO: 17) | 60 | |
| Mouse GAPDH | TGTTTGTGATGGGTG TGAACC (SEQ ID NO: 18) | CATGAGCCCTTCCAC AATGC (SEQ ID NO: 19) | 60 | |

For RT-qPCR, cDNA was synthesized by using 0.5 µg of total RNA with a SuperScriptIII® Cells Direct cDNA Synthesis kit (Bioneer, Inc, Daejeon, Republic of Korea). The levels of IL-18, cyclin D1, cyclin A1, caspase-3 and 7 mRNA were amplified in triplicate using the SYBR-Green® Real-time PCR master mix (Biotool LLC, Houston, Tex., USA) on a LightCycler®480 Real-Time PCR system (Roche, Basel, Switzerland). The level of glyceraldehyde-3-phosphate dehydrogenase (GAPDH) mRNA was used as an internal control in all the experiments. The primer sequences are listed in Table 2. The qPCR program was set to an initial denaturation at 94° C. for 2 min; then 40 cycles of denaturation at 94° C. for 10 sec, annealing at 60° C. for 15 sec, and extension at 72° C. for 30 sec; and a final extension at 72° C. for 5 min. The relative levels of gene expression were quantified by using the comparative CT method of $^{-\Delta\Delta}Ct$ (Livak and Schmittgen, 2001).

Cancer Cell Membrane Damage with Fluorescent Microscopy

MCF-7 cell changes after treatment of chicken cathelicidins peptides was determined by incubating $5\times10^3$ cells/well. Fluorescent microscopy (Nikon, Carl Zeiss, Oberkochen, Germany) was used to observe the membranes and cell contents changes after staining with DAPI and PI for 1 hour, after which 10 µl of stained solution was added to the glass slide in dark area. This was then covered with a cover slip to observe the damaged Mcf7 cells membranes after synthetic Nk-lysin peptides were used to treat them.

In Vivo Experiments

The Ehrlich Tumor Cell Inoculation

The Ehrlich ascites cells (EAC) were supplied by Faculty of Pharmacy of male in King Abdulaziz University, Jeddah. The transplantation of EAC cells in the mice was implemented based on the technique adopted by Frajacomo et al (Frajacomo et al. 2016). Ascitic fluid from EAC-bearing stock mice containing 8-10 days of ascitic tumor was obtained from the EAC cells. In order to cause carcinoma in mice for the experimental study, 9.9 ml of saline (dilution 1:50) was applied to 0.1 ml of EAC aliquot aspirated from stock mice and 0.1 ml of this diluted EAC ($1\times10^6$ cells) was subcutaneously injected into the back of 28 mice for the experimental study.

In Vivo Treatment

A total number of 35 male BALB/c mice were randomly divided into five groups (n=7/each) as follows: the first group as negative control, the second group was the positive control with mice bearing carcinoma and finally three groups with mice bearing carcinoma and treated with three different dose of chicken cathelicidin-1 of 10, 20 and 40 µg/ml. All Administration was given after two days of tumor implantation and for three times a week. The administration injected was intravenously (IV) and locally (at tumor site) simultaneously and the doses determined according to the mice body weight.

Tumor Volume Measurement

Tumor volume was measured by caliper digital after six days of tumor induction in mice groups and every two days. The volume of tumor was calculated using the following formula: $V_T = L \times W^2 \times 0.52$; where W is tumor width and L is tumor length. In addition, the tumor size of five mice in each carcinoma group was measured at second and third week via ultrasounds device (Vevo 2100 Imaging System®, Canada) with the following equation: $V_T = W \times L \times H \times 0.523$; where W is tumor width, L is tumor length, and H is tumor Height.

Measurement of INF-γ and TNFα by Flow Cytometry

Blood samples from each mouse were collected from the eyes by Sino-orbital puncture of mice using micro-capillary tubes. Blood samples were stored in clean and dry test tubes that contained ethylene diamine tetra acetic acid (EDTA). Red blood lysed with 1 ml of 1× BD FACS™ lysing solution (BD Bioscience, USA) for 10 minutes at room temperature and centrifuge at 500×g for 5 minutes, discard the supernatant and re-suspend the pellet in 3 ml of PBS. We performed cell count and viability analysis with hemocytometer. Cells were transferred to FACS tubes (BD Bioscience, USA) and performed surface staining with 5 µl of mouse mAbs that are specific for mice epitopes: PerpCP anti-CD3 (BD Bioscience, USA) and FITC anti-CD56 (Abcam, UK) for 30 minutes in the dark at room temperature, following fixed the cells with 100 µl of fixation buffer and permeabilized with 100 µl of Intracellular staining perm buffer. We performed intracellular staining with 5 µl of APC anti-TNFα (BD Bioscience, USA) and PE anti-INF-γ (BD Bioscience, USA) for 30 minutes in the dark at room temperature. Flow cytometry was executed on an LSR III (BD Biosciences, USA) using Diva® software.

Animal Survival

Mice were euthanized after three weeks of treatment. The animals were monitored daily upon $21^{th}$ day of tumor induction for signs of mortality. At the end of the experiment, the number of animals living in each group was determined and the survival percentage in each group was compared.

RNA Extraction, cDNA Synthesis and qPCR Analysis

Total cellular RNA was isolated from blood using GENE-JET® RNA purification kit (Invitrogen, USA) according to manufacturer's instructions. Total RNA concentration and purity were evaluated by measuring absorbance at 260 and 280 nm respectively, in a DeNovix DS-11™ microvolume spectrophotometer (NanoDrop 2000, Thermo Fisher Scientific, USA). First strand supplementary DNA (cDNA) was synthesized from 1 µg of total RNA sample using the first strand cDNA synthesis kit (Promega, USA) transcription system according to the manufacturer's conventions. Each reverse transcriptase (RT) reaction was incubated in thermal cycler (Applied Biosystem, USA) for 5 mins at 25° C., 60 mins at 42° C., 15 mins at 70° C., and finally was kept on hold at 4° C. The resulting cDNA samples were then stored at −20° C. Real-time polymerase chain reaction (PCR) amplification and analysis were performed in optical 48-well plates in Real-Time PCR Detection System (Applied Biosystem, USA) using SYBR® Green Master Mix (Qiagen, Germany) The intensification protocol comprised 40 cycles (denaturation at 95° C. for 15 s, annealing at 60° C. for 30 s, and extension at 72° C. for 30 s). The primers used for amplification of mouse granzyme B, mouse granzyme K and mouse Glyceraldehyde 3-phosphate dehydrogenase (GADPH) as housekeeping gene to normalize the expression data are depicted in Table 2. Results were calculated by the difference between Ct value of gene of interest and Ct value of housekeeping gene. While ΔΔCt was obtained by the difference between Ct value of treated and control groups. Finally, $2^{-\Delta\Delta Ct}$ was determined to represent the fold expression difference of gene of interest, between treated and control groups. $2^{-\Delta\Delta Ct} > 1$ indicates that gene expression in treated groups is higher than that in control groups.

Histological Analysis

Mice were anaesthetized by ether and sacrificed at the end of the experiment on day 21. Cancer tissues were extracted and fixed in 10% formalin and sliced into 5 µm thick sections, then washed, dehydrated, cleared, and embedded in paraffin wax. Deparaffinized sections through incubated slides at 65° C. for 30 minutes and immersed slides in xylene, two changes of 10 minutes each. Then rehydrated through immersed slides in two changes of 100% ethanol, 5 minutes each Immersed slides in 95% ethanol for two minutes, 70% ethanol for two minutes, 50% ethanol for two minutes. Rinsed slides in PBS for five minutes. Stained with 200 ul hematoxylin solution and incubated at room temperature for 5 minutes. Washed in distilled water and rinsed in PBS for 5 minutes. Stained with 400 ul of eosin solution for 30 seconds and washed with distilled water. Rinsed slides in PBS for 5 minutes. Dehydrated through 95% of ethanol, two changes of 5 minutes each and cleared in two change of xylene, 5 minutes each. The slides were mounted and prepared for light microscopic examination.

Immunohistochemistry Analysis

The paraffin blocks of cancer tissues were sliced into 5 μm thick sections and placed on positively charged glass slides, then incubated at 56° C. overnight, de-paraffinized in xylene, and placed for 10 minutes at room temperature. The excess liquid was drained, and the slides were then transferred to different concentrations of ethanol (100%, 90% then 70%). Slides were immersed in distilled water for one minute, followed by PBS for 5 minutes. Slides were immersed in 3% hydrogen peroxide for 5 minutes, followed by washing in PBS for 5 minutes. Ultra V block was applied and incubated for 5 minutes at room temperature to block nonspecific background staining. Slides were washed in PBS for 5 minutes. The anti-Bcl2 was applied to cover the tissue sections and the slides were kept in 37° C. for overnight. Slides were then immersed in PBS for 10-15 minutes. The slides were completely covered with biotinylated goat anti-polyvalent for 10 minutes at room temperature, immersed in PBS for 5 minutes and then completely covered with streptavidin peroxidase for 10 minutes, at room temperature. Slides were then immersed in PBS for 5 minutes, the chromogen was prepared by adding 1-2 drops (40 μl) DAB plus chromogen to 1 ml of DAB plus substrate, mixed by swirling. Tissue were completely covered with the chromogen for 10 minutes, at room temperature, rinsed with distilled water and the excess fluid was blotted around the tissues with filter paper. Tissue sections were counterstained with Mayer's hematoxylin, ready to use, for 5 minutes, followed by rinsing of slides with tap water, for 10 minutes. Dehydration of sections in ascending concentrations of ethyl alcohol (70%, 90%, and 100%) for 10 minutes each was done. The slides were immersed in xylene, mounted, and covered with cover slips.

Statistical Analysis

All data are expressed as the mean±standard deviation. Data analyses were performed using GraphPad Prism 9 (GraphPad Software, Inc., La Jolla, Calif., USA). Significance was determined using Student's t-test for two groups and one-way ANOVA for multiple comparisons. The Kaplan-Meier function was calculated for survival and a log-rank test was used to assess the differences of mice survival. $P<0.05$ was considered to indicate statistically significant differences.

Results

The main objective of this study was to examine the in-vitro inhibition of breast and colon cancer cells under the effect of chicken antimicrobial peptides (chicken cathelicidins-1, -2, and -3) besides examining the mechanism of action behind the stimulation of program cell death and processes preventing cancer-cell from undergoing cell division. An in vivo investigation was achieved to evaluate the role of chicken cathelicidin in Ehrlich ascites cell (EAC) suppression as a tumor model after subcutaneous implantation in mice. Several parameters in blood lymphocytes and tissues were investigated to study the possible therapeutic antitumor immunity effects of chicken cathelicidin on a carcinoma animal model.

In Vitro Experiments

Breast and Colon Cancer Cell Lines Cytotoxicity

As per our study, the rate of inhibition of cancer cell growth at lower concentration (10 μg/ml) of chicken cathelicidins was between 66% and 85%. As the concentration of chicken cathelicidins peptides was changed to moderate level (10 μg/ml), there was a significant decline in the rate of cell survival. FIG. 1 shows that as the concentration was increased to a high level (40 μg/ml) and observations were made at 24 h of treatment, a dramatic decrease in growth was seen in the cancer cell line.

When the cells were observed after 48 h of low concentration (10 μg/ml) peptide treatment, they depicted 25% survival rate for chicken cathelicidins-1, 64% for chicken cathelicidins-2 and 58% for chicken cathelicidins-3. When treated for 48 h with moderate concentration (10 μg/ml) of peptides, the treated cells showed survival rates of 12% for cathelicidins-1, 64% for cathelicidins-2 and 31% for cathelicidins-3. Considering the treatment with 40 μg/ml of cathelicidin, there was a sharp decline of about 7% in the cell growth of both cell lines for cathelicidin-1 and cathelicidin-3 while 10% decline was observed in cell growth after 48 h long treatment with cathelicidin-2.

It became evident from the study outcomes that at the time interval of 72 h of treatment, cancer cells depicted a development rate of 43% and 48% for cathelicidin-1, 61.3% and 72% for cathelicidin-2 and 65% and 73% for cathelicidin-3 for both HCT116 and MCF-7 cell lines respectively, while the concentration of each peptide was low. On the other hand, as the peptide concentration was increased from low to moderate (20 μg/ml), we observed a decline in cancer cell growth at the time interval of 72 h of treatment with 23.8% and 22% development rate for chicken cathelicidin-1, 24% and 44% for chicken cathelicidin-2, and 43.5% and 73% for chicken cathelicidin-3 treatment for both HCT116 and MCF-7 cell lines, respectively. This shows that cancer cell growth was significantly inhibited (around 85-95%) when treated with high concentration of chicken cathelicidins (40 μg/ml) at 72 h of treatment for both HCT116 and MCF-7 cell lines, respectively, proving the cathelicidins to be strong anti-cancer agents.

Expression Levels of Cyclin A1 and Cyclin D1

Figure 2A:
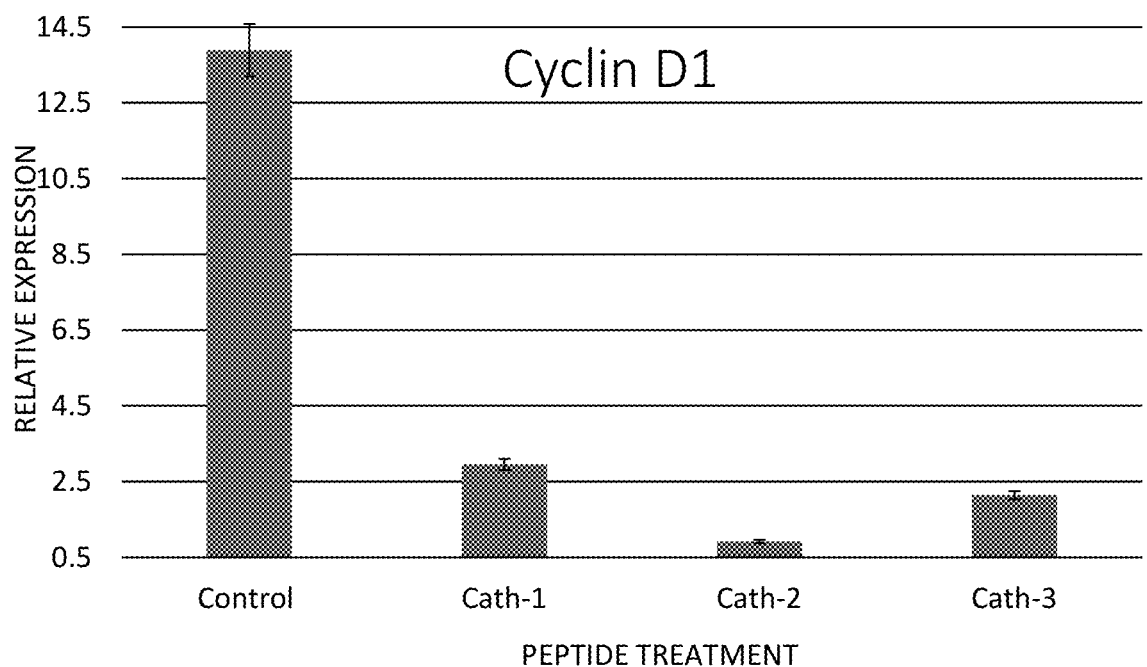
FIGS. 2A-B. The expression patterns of (A) Cyclin D1 and (B) Cyclin A1 genes after challenge with chicken cathelicidin peptides and untreated cell (Control). The expression levels were normalized to glyceraldehyde-3-phosphate dehydrogenase as the reference gene. All assays were performed in 3 independent experiments, and each point is the mean±SD. The baseline is 1 or −1, since the range is defined to be between +X and +1 for the up-regulated genes, and between −1 and −X for the down-regulated genes.
Figure 2B:
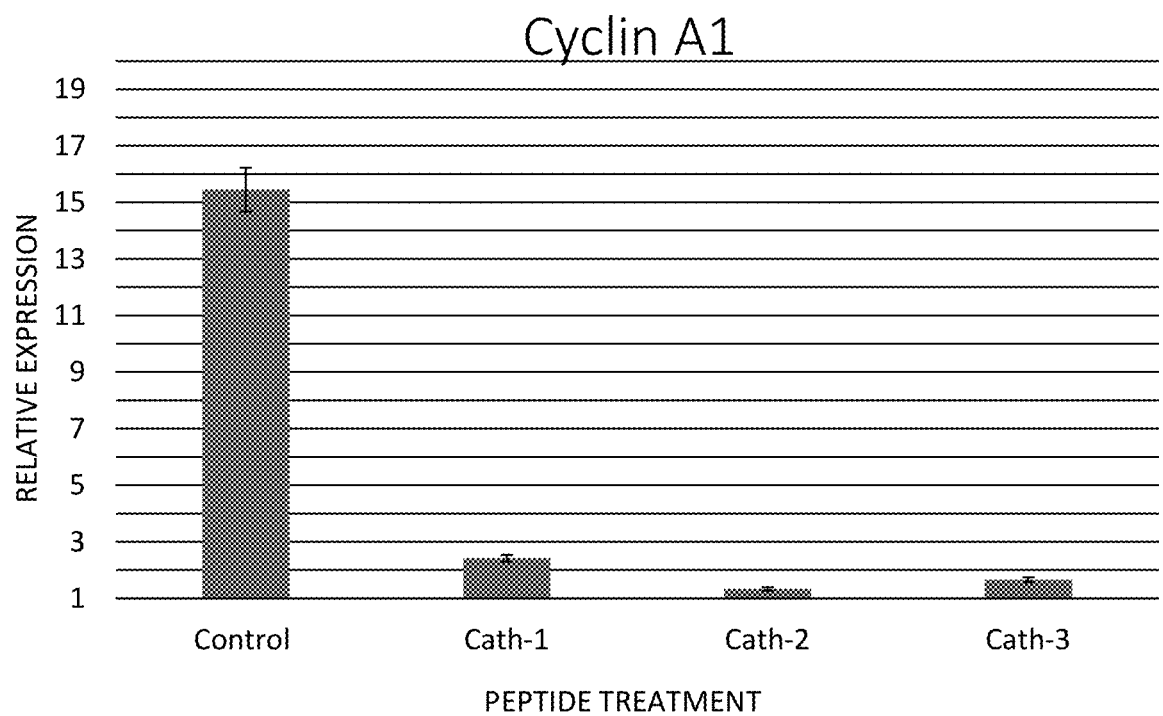

FIGS. 2A-B depict the change in cyclin A1 gene and cyclin D1 gene expression after subjecting the breast cancer cell line to chicken cathelicidins. Cyclin A1 and Cyclin D1 are the genes associated with cell cycle division. It was found that the untreated cells (MCF-7 control) show expression of both the genes while cells treated with chicken cathelicidins peptides do not depict clear expression of these genes. The cells treated in this way may sometimes even depict cell cycle division arrest in the cell cycle phases of G1/S and G2/S (prometaphase arrest) consequently inhibiting the growth of the breast cancer cell line and ultimately causing death of cancer cells. All the chicken cathelicidin peptides showed similar outcomes in terms of reducing the cancer cell survival.

Expression Levels of Caspase-3 and -7

Figure 3A:
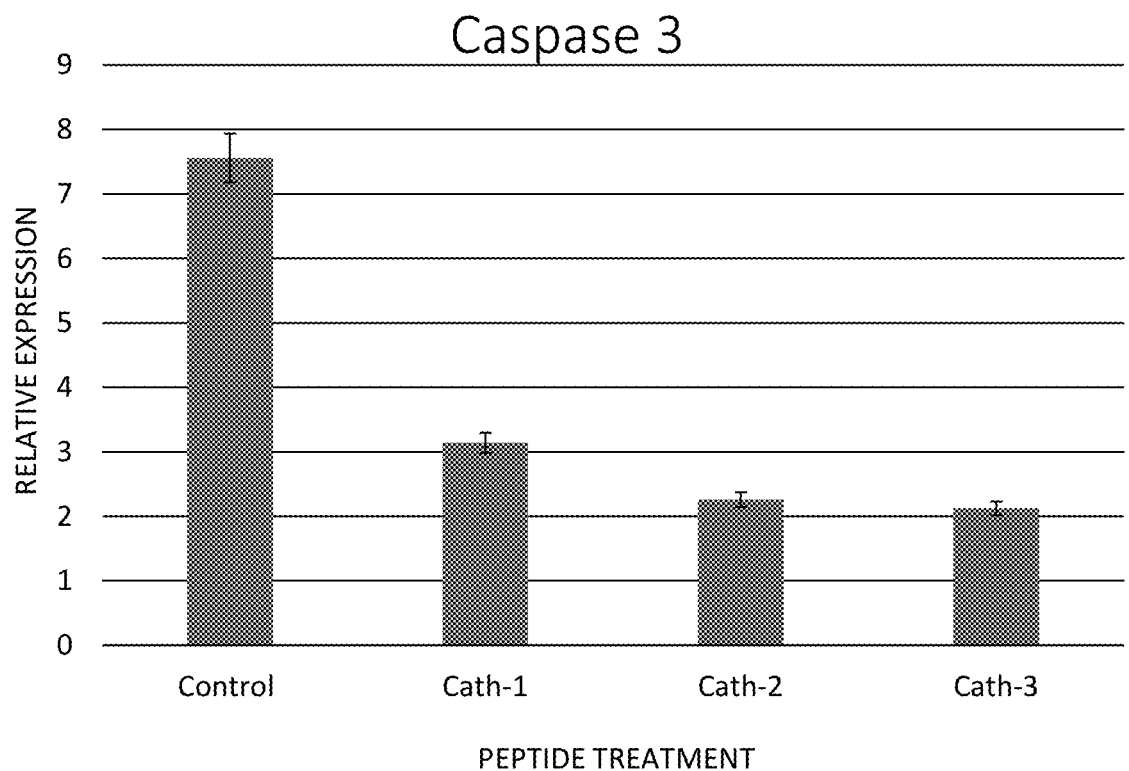
FIGS. 3A-B. The expression patterns of (A) caspase-3 and (B) caspase-7 genes in MCF-7 cells after challenge with chicken cathelicidin peptides and untreated cell (Control). The expression levels were normalized to glyceraldehyde-3-phosphate dehydrogenase as the reference gene. All assays were performed in 3 independent experiments, and each point is the mean±SD. The baseline is 1 or −1, since the range is defined to be between +X and +1 for the up-regulated genes, and between −1 and −X for the down-regulated genes.
Figure 3B:
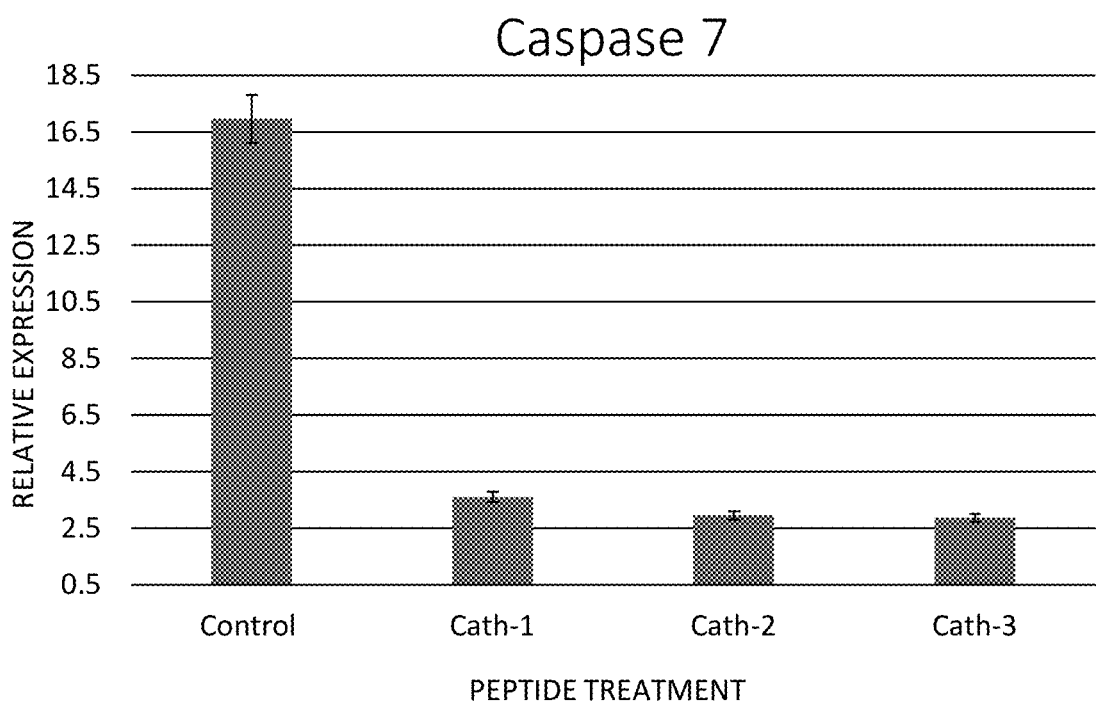

The MCF-7 cells treated with chicken cathelicidin peptides were then subjected to RT-PCR testing in order to determine the patterns of expression of the Caspase-3 gene and Caspase-7 gene associated with cysteine protease family. It is recognized that these genes are responsible for mediation of apoptotic pathways through the execution of intracellular proteins associated with cytoskeleton protein fibres. In this context, FIGS. 3A-B show that cathelicidin-1 induced a detectable level of caspase-3 gene expression which was 3 times greater than the expression of this gene in untreated cells whereas, treatment with cathelicidin-2 and -3 induced two times greater gene expression. The treatment with cathelicidin-2 and -3 resulted in two-fold caspase-7 gene expression than the expression of this gene in untreated MCF-7 cells. However, treatment of cancer cells with cathelicidin-1 did not show any change in caspase-7 gene expression.

Cell Membrane Morphology

The changes caused by chicken cathelicidin peptides in the morphology and survival of breast cancer MCF-7 cells were determined with the help of DAPI and PI dyes. These dyes are used to distinguish between living and dead cells on the basis that they have the ability to stain dead cells while they cannot cause any staining in live cells due to impermeability in such cells. Fluorescent microscopy was used to determine the extent of damage caused by cathelicidin peptides to the membranes of MCF-7 cells.

The outcomes of our study indicated that before the treatment of MCF7 cells with peptides, the membranes of these cells were not disrupted; however, when the breast cancer cells were subjected to chicken peptide, bright staining was evident in most of the cells indicating greater stain permeability post-treatment in comparison to untreated MCF-7 cells. Moreover, the shape of the mitochondria in treated cells is also elongated due to the effect of peptides on mitochondrial membrane. The nucleus of the treated cells undergoes fragmentation and is also smaller in size than in untreated cells.

In Vivo Experiments

Figure 4A:
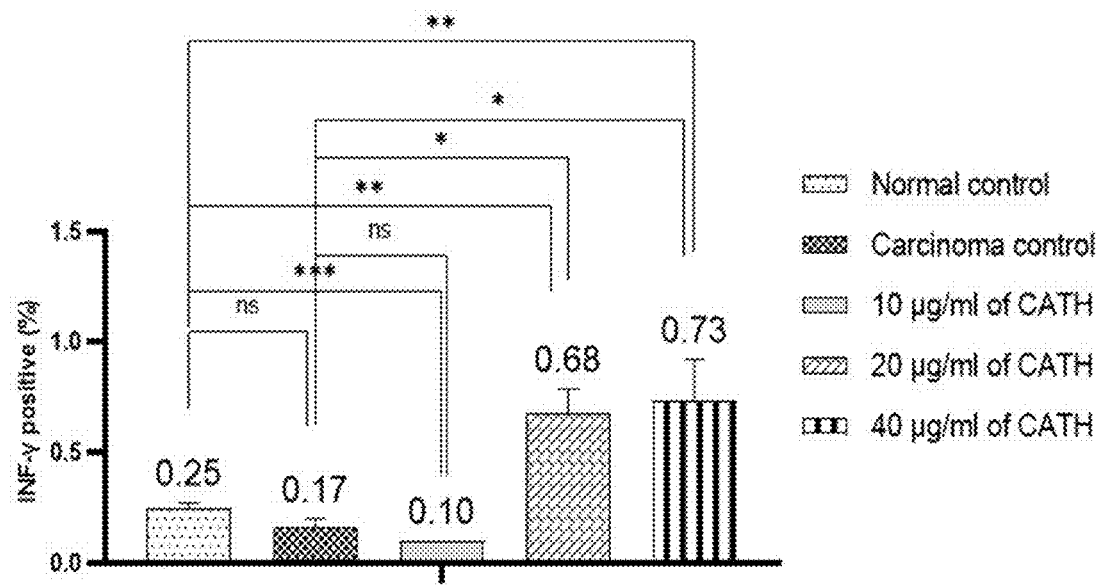
FIGS. 4A-B. Flow cytometric analysis of (A) INF-γ and (B) TNFα population percent of mice groups. Values are given as mean±SD; n=7 per group. ns: non-significant, *P<0.05, P<0.01, *P<0.001 compared to control groups).
Figure 4B:
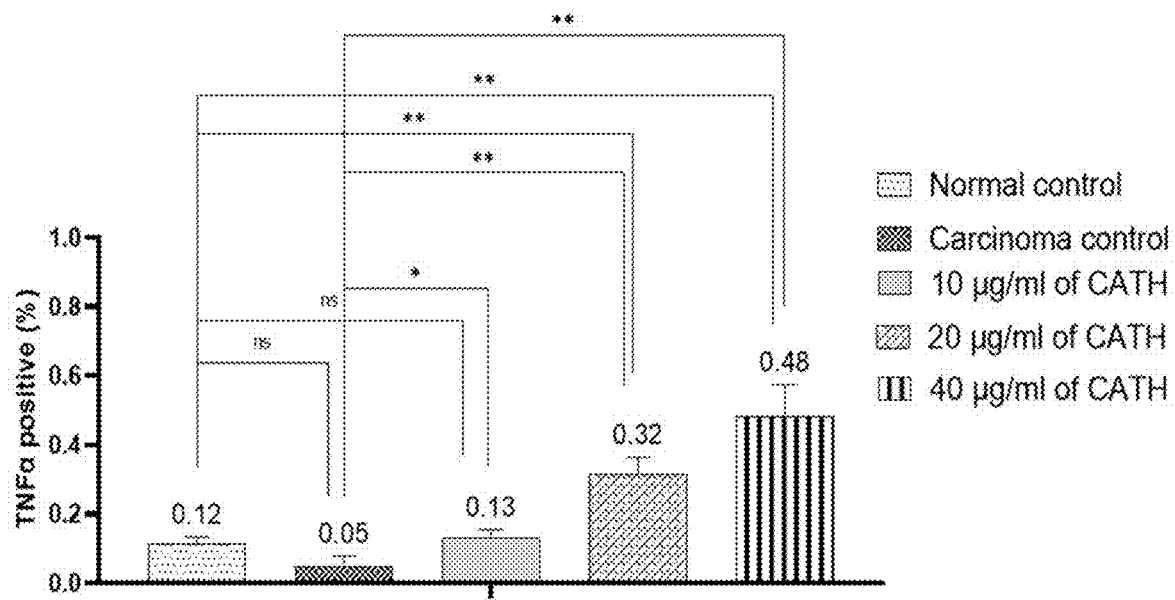

The Level of INF-γ and TNFα Population after Chicken Cathelicidin Administration Our results indicated that the level of INF-γ was significantly increased in groups treated with 20 & 40 μg/ml of CATH-1 (0.67±0.11) (0.73±0.18) respectively when compared to that of normal mice (0.25±0.02, $P=0.0017$, $P=0.0064$) respectively and carcinoma group (0.16±0.03, $P=0.0128$, $P=0.0397$) respectively as shown in FIG. 4A. Meanwhile, the INF-γ level was significantly decreased in the group treated with 10 μg/ml of CATH-1 (0.1±0) in comparison with normal mice (0.25±0.02, $P=0.0007$). On the other hand, the level of INF-γ was non significantly different in mice treated with 10 μg/ml of CATH-1 (0.1±0) as compared to carcinoma control mice (0.16±0.03, $P=0.0624$). A similar trend was found in the level of TNFα which showed a significant increase in mice treated with 20 & 40 μg/ml of CATH (0.3±0.05) (0.4±0.1) respectively as compared with that of the normal mice (0.12±0.01, $p=0.0027$, $P=0.003$) respectively and untreated carcinoma mice (0.05±0.02, $P=0.0031$, $p=0.0057$) respectively. Moreover, TNFα showed a significant increase in mice treated with 10 μg/ml of CATH (0.1±0) in comparison with that of the untreated carcinoma group (0.05±0.02) ($P=0.0438$). While the TNFα showed a non-significant different in mice administered 10 μg/ml of CATH-1 (0.1±0) compared to normal group (0.12±0.01, $P=0.0630$) as noted in FIG. 4B.

Changes in Tumor Volume after Chicken Cathelicidin Administration

Figure 5:
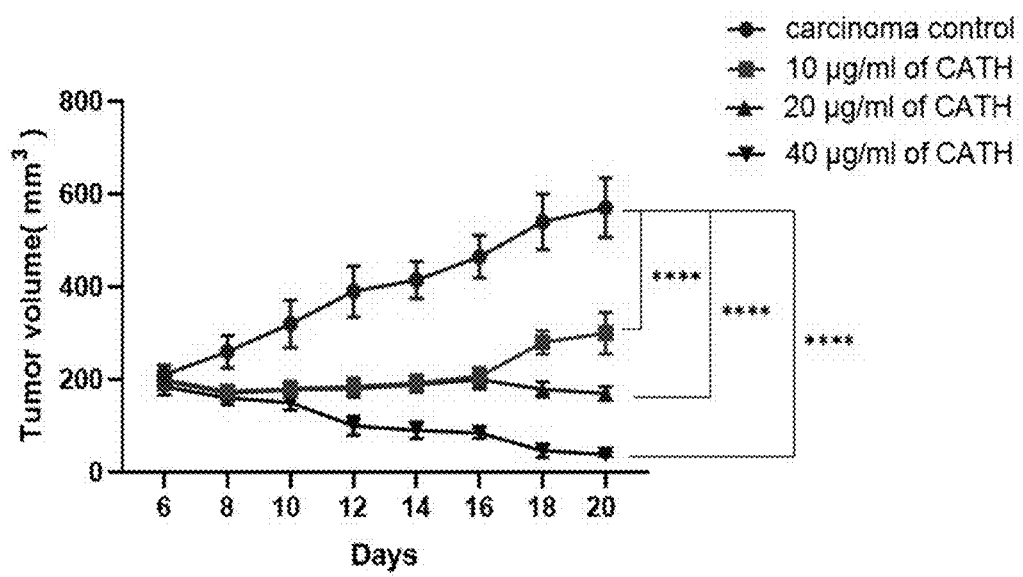
FIG. 5. Tumor volume of EAC-bearing mice groups. Values are given as mean±SD; n=7 per group. (****p<0.0001 compared to untreated carcinoma control groups).

FIG. 5 represents the effect of treatment with CATH-1 on tumor growth through 21 days. The figure shows the changes of tumor volume of mice measured by calliper in each group during the in vivo experiment. The tumor volume of mice in each group was significantly different, and the tumor volume of mice treated with CATH-1 (10, 20, & 40 μg/ml) was significantly smaller than of the carcinoma control ($p<0.0001$).

The high-frequency ultrasound technique was used to calculate the tumor volume from ultrasonography measurements (three diameters) at the second and third week after tumor transplantation and dose administration. We scanned five mice in each group via ultrasound and some follow up mice died, so we got an equal number of mice in each group (three mice per group). The size of tumor in untreated EAC-bearing was elevated at third week by 85.19, 79.13 and 115.97 mm$^3$ respectively. On the other hand, the tumor volume of treated EAC-bearing mice with different concentration of CATH-1 (10, 20 & 40 μg/ml) showed a decrease in tumor volume at the third week. The group treated with 10 μg/ml of CATH-1 exhibit a decrease in tumor size by 147.12, 144.53 and 194.51 mm$^3$ respectively. In addition, group treated with 20 μg/ml of CATH revealed a decrease in tumor size by 158.78, 72.89 and 230.15 mm$^3$ respectively. Similarly, mice treated with 40 μg/ml of CATH-1 showed a decrease in tumor size by 53.92, 43.92 and 57.98 mm$^3$ respectively.

Figure 6:
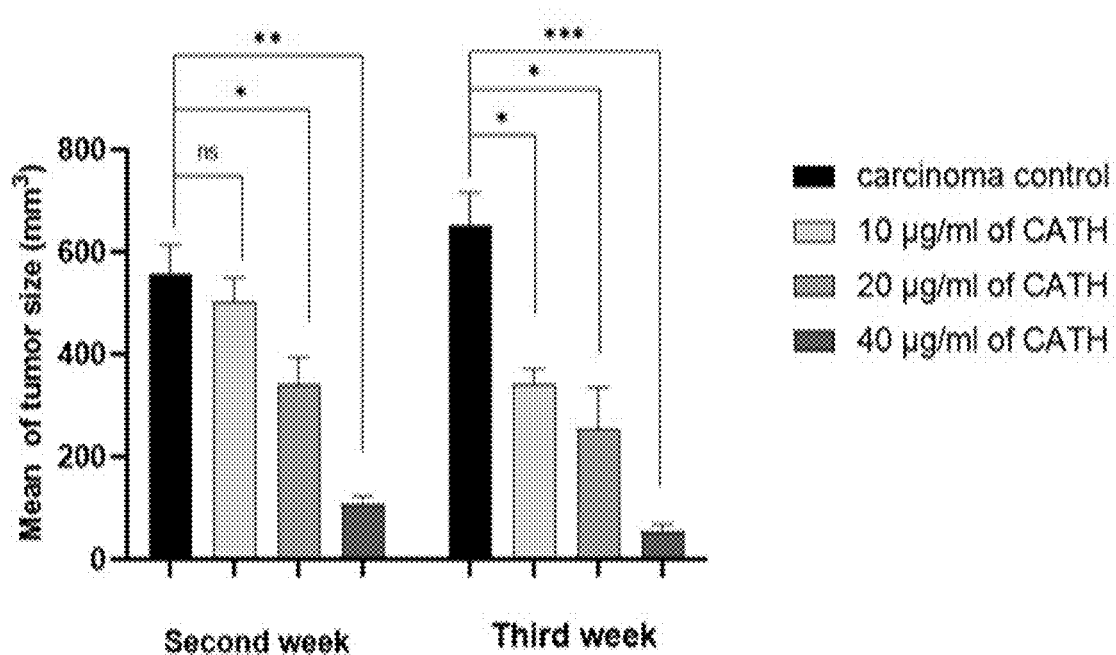
FIG. 6. Mean of tumor size of tumor mice groups measured by ultrasound imaging. Values are given as mean±SD; n=3 per group. (ns=non-significant, *p<0.05, p<0.01, *p<0.001).
Figure 7:
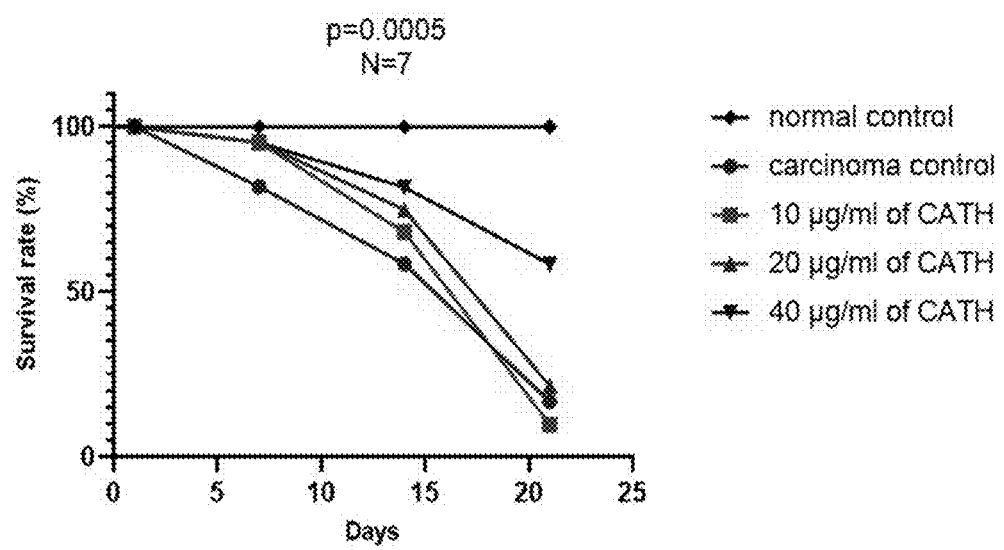
FIG. 7. Survival rate of mice groups. Kaplan-Meier survival curves were used to estimate survival rate in five groups (n=7). Survival rate differences were analyzed by the log-rank test.

The results revealed that no significant difference in tumor size in mice group treated with 10 μg/ml of CATH-1 at second week (502.77±47.02) as compared with carcinoma control (558.37±55.005, $P=0.485$). While the tumor size of mice given 10 μg/ml of CATH-1 showed a significant decrease at third week (340±30.97) in comparison to untreated carcinoma control (651.79±64.53, $P=0.012$) as depicted in FIG. 6. The mice treated with 20 μg/ml of CATH-1 showed a significant decrease in tumor size at second week (342.42±51.33) and third week (255.08±79.68) as compared to untreated tumor mice at second week (558.37±55, $P=0.045$) and third week (651.8±64.53, $P=0.018$). Similarly, tumor size in mice taken 40 μg/ml of CATH-1 showed a significant decrease at second week (107.55±16.43) and third week (55.61±12.79) as compared to carcinoma mice at second week (558.37±55, $P=0.0014$) and third week (651.8±64.53, $P=0.0008$). Additionally, the untreated EAC-bearing mice and mice receiving a dose of 10 μg/ml of CATH-1 showed high rate of death, whereas the mice treated with 40 μg/ml of CATH showed high survival rate as indicated in FIG. 7.

Figure 8A:
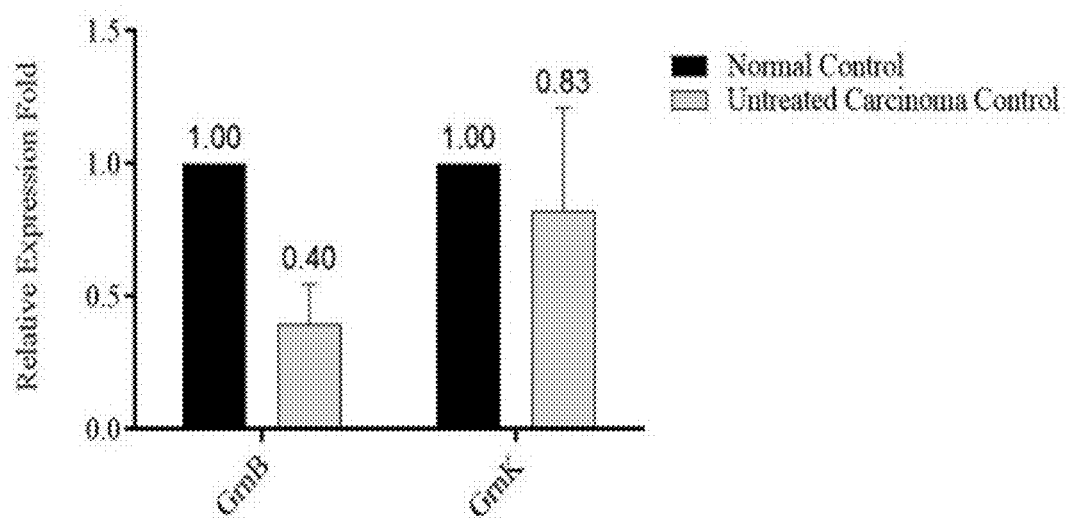
FIGS. 8A-B. Expression level of granzyme B (GrnB) and granzyme K (GrnK) after chicken cathelicidin administration. Data was plotted using the $2^{-\Delta\Delta Ct}$ method (expression normalized to the house keeping gene GADPH). Fold expression and significance was calculated relative to control groups. Data presented as mean±SD; n=7 in each group. (***p<0.001 compared to control groups).
Figure 8B:
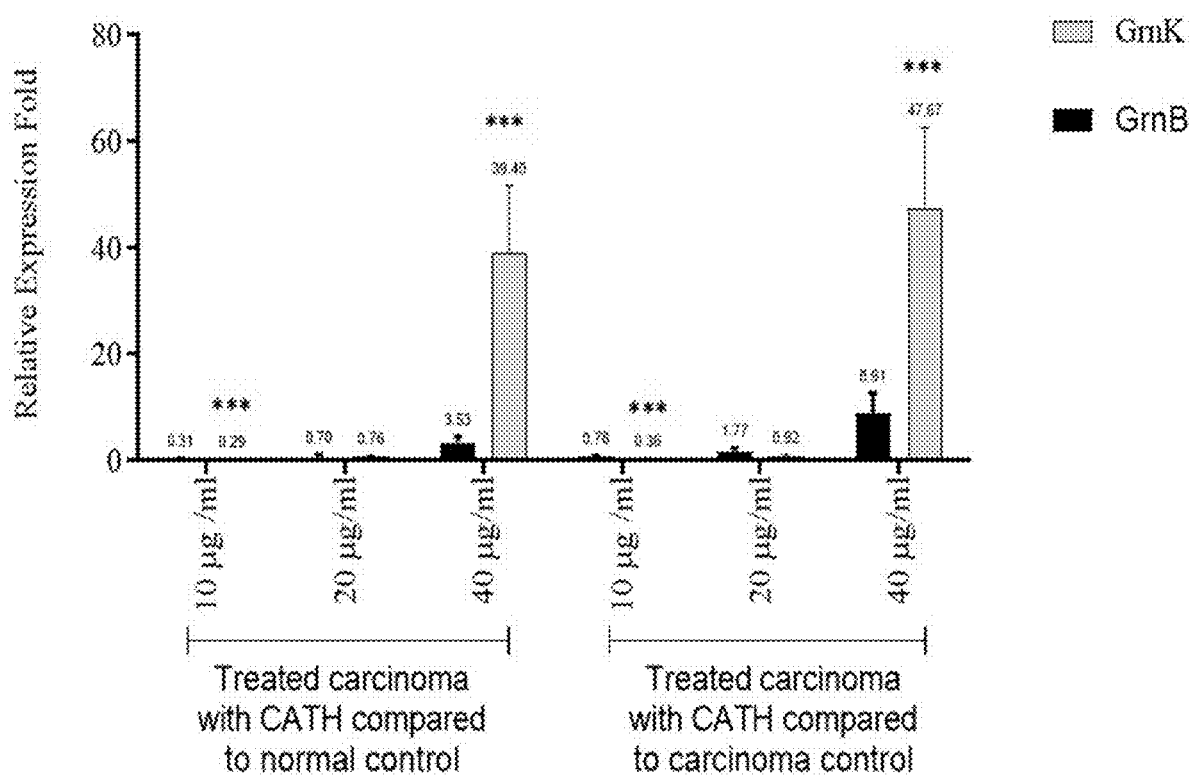
Figure 9A:
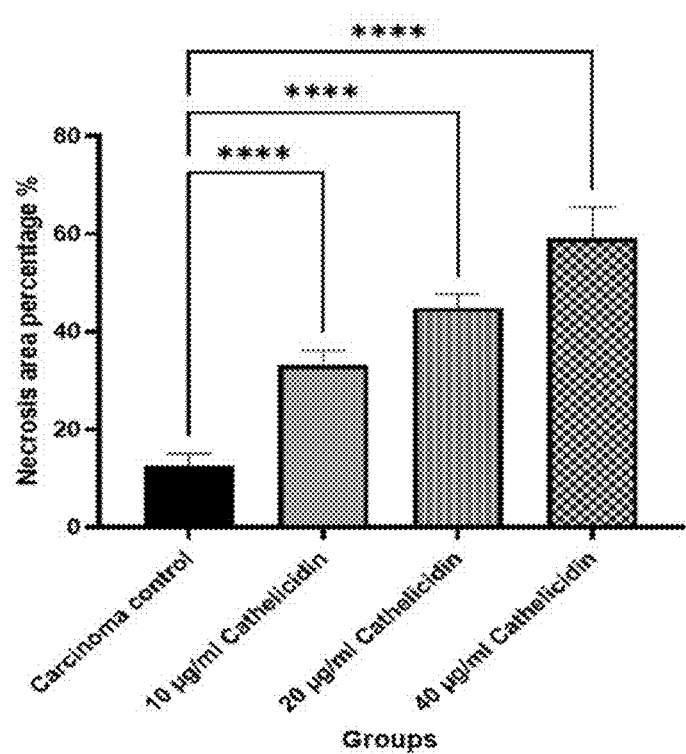
FIGS. 9A-D. Column chart demonstrating the mean (A): Necrosis area percentage %, (B): Necrosis area score, (C): Giant cell score, and (D): Mitotic Figure score. Data were expressed as mean±standard error (S.E.), N=number of the mice in each group, One-way ANOVA followed by Bonferroni's post-hoc analysis comparison tests. Non-significant (ns), P<0.01, *P<0.001, ****P<0.0001.
Figure 9B:
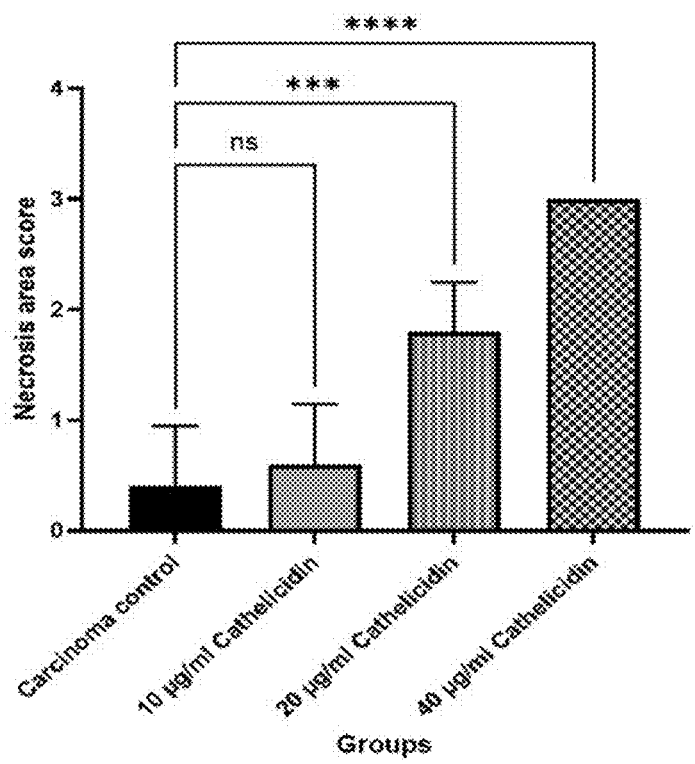
Figure 9C:
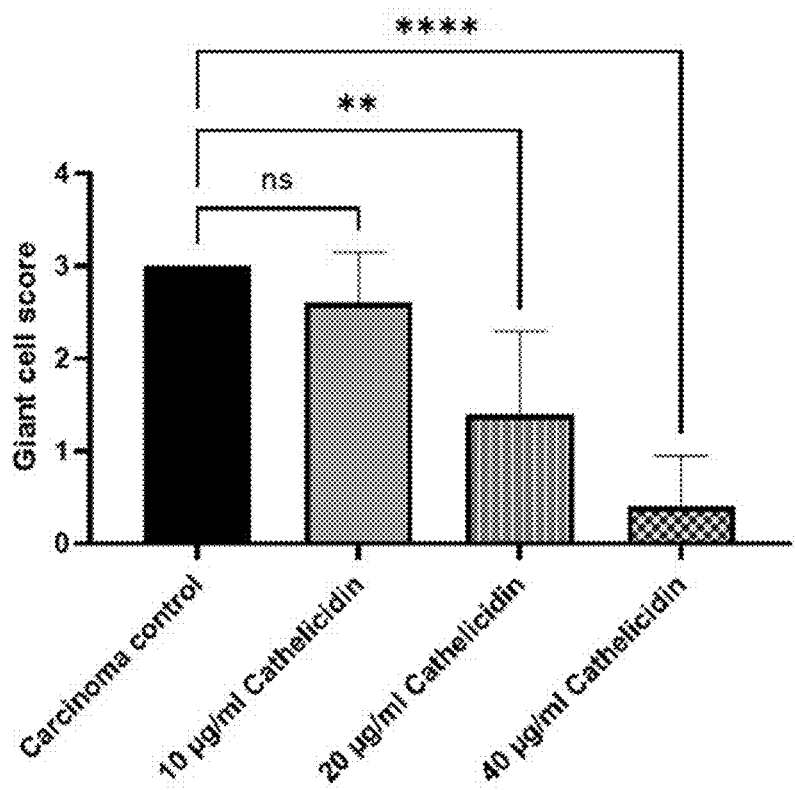
Figure 9D:
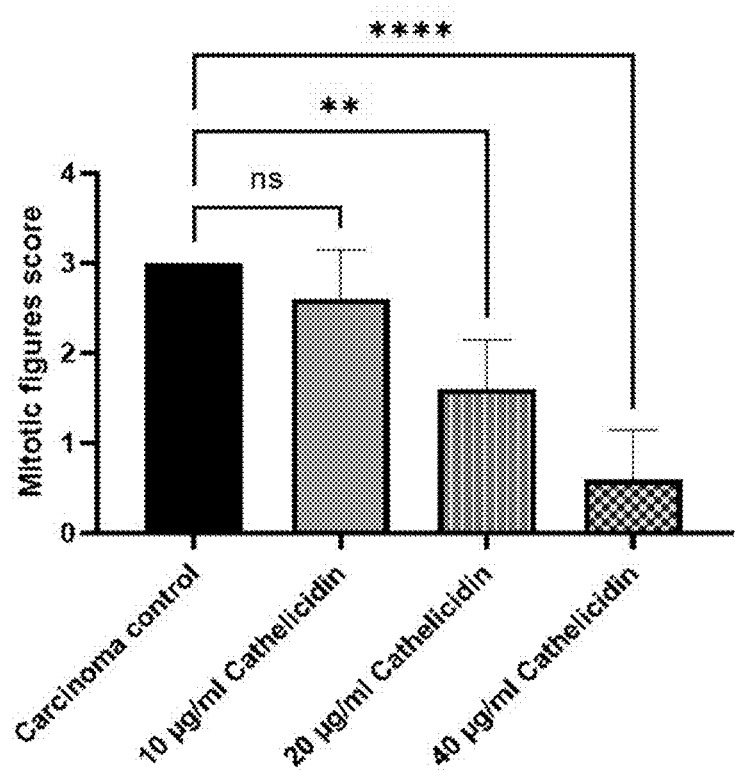

The Level of Expression of Granzyme B and K after 4 Chicken Cathelicidin Administration As shown in FIG. 8, exposure to cathelicidin at a concentration of 40 μg/ml significantly increased granzyme K expression by (39.3±12.4) (47.6±15) fold in comparison to normal mice and carcinoma mice respectively. However, there was a significant decrease in granzyme K expression in EAC-bearing groups treated with 10 μg/ml of cathelicidin by (0.36±0.1) (0.293±0.1) fold as compared to normal mice and carcinoma control, respectively. In addition, cathelicidin did not affect expression of granzyme B in mice groups.

Histological Examination

Subcutaneous implantation of Ehrlich tumor cells resulted in the development of Ehrlich solid tumor. The hematoxylin & eosin staining sections prepared from solid tumors of the untreated control group showing high-grade malignant growth formed with minimal foci of necrosis. Ehrlich solid tumor showed large, round, and polygonal cells, with pleomorphic shapes, hyperchromatic nuclei, and binucleation. In addition, several degrees of cellular, nuclear mitotic figures, and scattered giant cells with multiple nuclei were also observed. Some areas showed multiple malformed, widely dilated blood vessels (angiogenesis) were seen in the surrounding tissue with leukocyte infiltration.

Based upon histopathology results, cotreatment of Ehrlich solid tumor with 10 μg/ml of CATH-1 revealed mild wide zones of necrosis and cells with mitotic figures, and few giant cells in between inflammatory cell infiltrations. The 20 μg/ml of CATH-1 treated groups showed a moderate focal area of necrosis. Interestingly, the histopathological pictures showed improvement in mice given 40 μg/ml of CATH-1 as evidenced by increasing necrosis degrees and most of the cells showing apoptosis progressively and most cells appeared with chromatin dust and fragmented nuclei.

Necrosis Area Percentage % and Histological Scoring for Solid Tumors

Histopathological analysis has been carried out of tumor sections with an emphasis on necrotic proliferation, characteristic mitotic feature, and neoplastic gigantic cell presence. Blindly examined and their frequency and strength were measured: (0) absent, (1) weak to mild, (2) mildly to moderately and (3) strong or regular histopathologic inspection. In the present study, there was a significant increase in the necrosis area percentage in the group treated with 10 μg/ml of CATH-1 (33.20±1.31), the group treated with 20 μg/ml of CATH (44.80±1.31), and the group treated with 40 μg/ml of CATH (59.00±2.91) as compared to Ehrlich solid tumor control ($P<0.0001$) (FIG. 9). In addition, the group treated with 10 μg/ml of CATH-1 showed a non-significant difference in the score of the necrosis area (0.60±0.24), Giant cell (2.60±0.24), Mitotic figures (2.60±0.24) as compared to solid tumor control ($P>0.05$). Interestingly, the group treated with 20 μg/ml of CATH exhibited a significant increase of score of the necrosis area (1.80±0.20) as compared to the tumor control group ($P<0.001$) and showed a significant decrease in the score of giant cells (1.40±0.40) and mitotic figures (1.60±0.24) as compared to carcinoma control group ($P<0.01$).

Moreover, the group treated with 40 μg/ml of CATH-1 showed a significant increase of score of the necrosis area (3.00±0.00) as compared to tumor control group ($P<0.0001$) and showed a significant decrease in the score of giant cells (0.40±0.24) and mitotic figures (0.60±0.24) as compared to the carcinoma control group ($P<0.0001$).

Immunohistochemical Investigation

Figure 10:
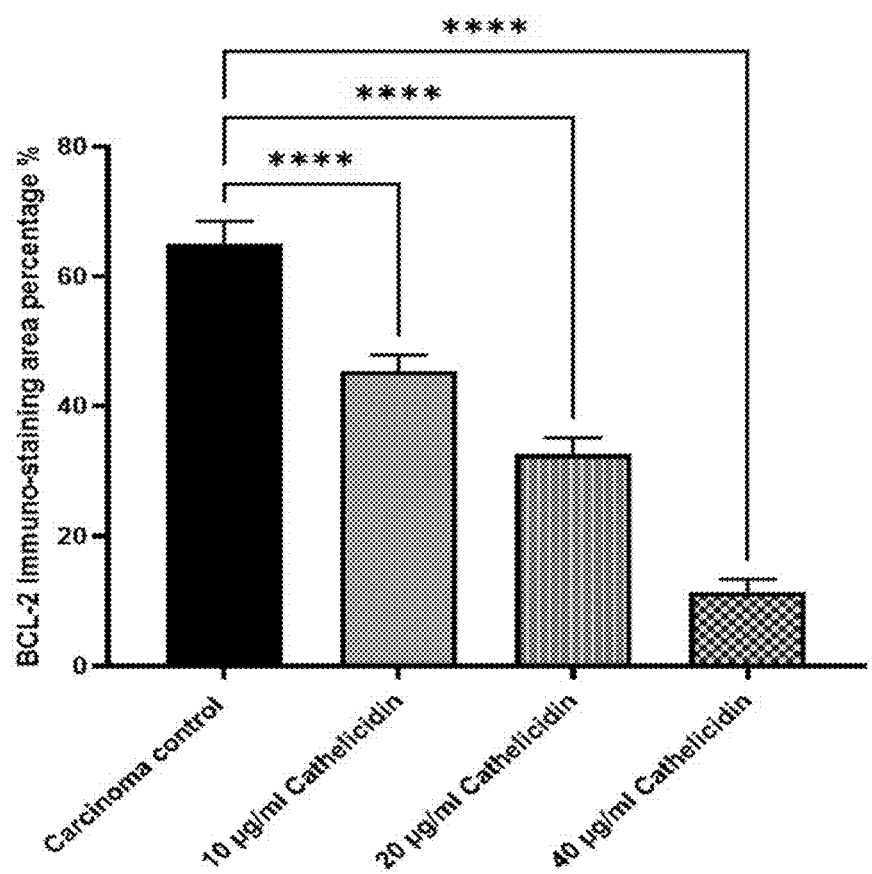
FIG. 10. Column chart demonstrating the mean area percentage of BCL-2 immunohistochemical staining for solid tumors grown in mice groups. Data were expressed as mean±standard error (S.E.), N=number of the mice in each group, One-way ANOVA followed by Bonferroni's post-hoc analysis comparison tests. ****P<0.0001.

Antiapoptotic Bcl2 expression was detected in tumor sections in untreated Ehrlich solid tumor control and Ehrlich cotreated with different doses of CATH-1(10, 20 & 40 μg/ml). The tumor section in the Ehrlich solid tumor untreated control group exhibited a strong positive reaction for Bcl2 expression. In contrast, mild to moderate positive reactions for Bcl2 expression were detected in Ehrlich cotreated with 10 & 20 μg/ml of CATH-1. Interestingly, in cotreated group with 40 μg/ml of CATH-1 showed few positive cytoplasmic brownish reactions for Bcl2 between extensive negative cells. The immune-staining analysis was achieved and summarised in FIG. 10. There was a significant increase of the antiapoptotic BCL-2 in solid tumors grown in mice in control group (65.00±1.58) as compared to the group treated with 10 μg/ml of CATH (45.40±1.12, $P<0.0001$), the group with 20 μg/ml of CATH (32.60±1.12, $P<0.0001$), and the group treated with 40 μg/ml of CATH (11.40±0.87, $P<0.0001$). Interestingly, a high dose of cathelicidin at 20 and 40 μg/ml revealed significant decrease of the BCL2 immuno-staining area percentage % for solid tumors as compared to control group ($P<0.0001$, $P<0.0001$, respectively).

Discussion

Various issues are prevalent with respect to cancer management. The first issue is the side-effects of the treatment methods used for cancer management. Cancer cells are subjected to cytotoxicity through a number of treatment strategies like radiation therapy, chemotherapy, or chemo radiotherapy (combination of the radiation and chemotherapy) (kuroda et al., 2015; Higgins et al., 2015; Urruticoechea et al., 2010). Besides these, cancer therapy may involve using RTK or kinase inhibitors or other specific inhibitors (available as small organic molecules or monoclonal antibodies) (Ciruelos, 2014; Vincenzi et al., 2015; Karczmarek and Salek, 2015). Despite the effective treatment of various cancer types through these interventions, the non-specific mechanisms of these interventions result in side effects and delayed neurotoxicity.

Resistance is the next issue faced during cancer therapy. Various factors may be attributed to resistance development. The main problem with traditional anti-cancer agents is that these are mainly focused on inhibiting cancer cell growth with no focus on tumor penetration. Consequently, the growth-arrested hypoxic cells inside tumors show a decline in their sensitivity (Ruan et al., 2009). Hence, innovative and more effective interventions are needed to be developed for cancer treatment. Various new cancer treatment targets have been recognized in numerous studies; these include mitochondria (Pathania et al., 2009), anti-angiogenesis (Li and Cozz, 2010) and hybrid tubulin-targeting compounds (Breen and Walsh, 2010). It is also possible to take cancer treatment to new heights by determining peptides that have anti-cancer properties and developing such peptides (Udenigwe and Aluko, 2012; Zheng et al., 2011; Smolarczyk et al., 2009).

This study served as the pioneer in studying the anticancer role of chicken cathelicidin peptides against different cancers in vitro and in vivo. The mechanism of action of the interaction of cationic peptides with breast cancer cell line MCF-7 was also investigated. The current study considered 3 different concentrations of peptides at 3 different time intervals to gain an insight into the anticancer impact of these peptides on breast and colon cancer cell lines MCF-7 and HCT116, respectively. It was found that exposure of cells to higher concentration of these peptides for 24 h led to about 95% inhibition of cell growth. At another time interval of 48 h of treatment, the treated cells showed lesser inhibition of cell growth; however, despite this reduction, there was adequate level of killing efficacy when the cells were treated with high concentrations of cathelicidin-1 and cathelicidin-3 peptides. These outcomes correspond to the outcomes of other studies that suggest that cytotoxic character of LL-37 and its fragments is evident in different types of cancer cells (Mader et al., 2009; Wu et al., 2010; kuroda et al., 2015).

It is important to consider that when the cells were subjected to incubation with chicken cathelicidin-1 for 72 h, the breast and colon cancer cell lines did not show any growth. Similarly, cells subjected to high concentration of cathelicidin-2 and -3 peptides also showed negligible growth of 7% and 16% accordingly. As per the outcomes, chicken cathelicidin-1 peptides outperformed both the other peptides in all 3 concentrations and all 3 time intervals in terms of its anticancer activity when treating both breast and colon cancer cell lines. The outcomes of our study showed correspondence with other works that indicate the contribution of human cathelicidin antimicrobial peptide LL-37 during carcinogenesis. Anticancer properties of the Cathelicidin LL-37 gene in humans and its fragments and counterparts are evident in various cancer cell lines (kuroda et al., 2015).

Various research works revealed therapeutic significance of a combination of human cathelicidin and oligo of Cytosine-phosphate-guanosine in terms of their antitumor properties during in-vivo experiments (50-100 µg/mL) (Chuang et al., 2008). The combination was also discovered by Chuang et al. to stimulate activation and division of NK (natural killer) cells; this causes more DNA translocation and consequently greater potential anticancer efficacy besides promoting the production of interferon-α in plasmacytoid dendritic cells (80). Hence, human cathelicidin plays a crucial role in the therapy of ovarian cancer by acting as a target as well as a candidate (kuroda et al., 2015). According to Lee et al. (2011), both bacteria and tumor cell cultures depicted higher cytotoxicity of the chicken Nk-lysin peptides and their derivatives following the incubation.

The role of high Tumor Necrosis Factor TNF expression in modulation of immune system was highlighted by Parvy et al. (2019). He discovered that when some of the tumor cells are treated, the phosphatidylserine (PS) develops sensitivity to the effects of tracheal and fat tissue secretions namely the *Drosophila* diptericin defensin; this exposure is mediated by TNF. *Drosophila* diptericin defensin stimulates cell death as well as regression of tumor by binding tumor cells in PS-enriched regions. Moreover, in vitro examinations showed stimulation of death of prostate and renal cancer cells with the expression of human beta-defensin-1 (Bullard et al., 2008; Sun et al., 2006). It was also found in other studies that the patients with prostate, lung or colorectal cancers showed reduced survival rate when there was prevalent deletion of human defensin gene (Ye et al., 2018). Another study pertaining to this subject of beetle defensin revealed the anticancer effect of a combination of this gene with synthetic peptides on certain cancers (Iwasaki et al., 2009). Peng et al. (2020a,b) concluded that chicken cathelicidin-2 and -B1 have both antibacterial and immunomodulatory roles when they incubated with chicken macrophages cell line infected by pathogenic *E. coli* through neutralisation of certain bacterium and decreased inflammation response.

Our study revealed that chicken cathelicidin peptides can indirectly lead to death of cancer cells. Without being bound by theory, the mechanism of action involves the action of these peptides on breast cancer cells to down regulate certain genes essential for G1/S phase transient and S/G2 phase in these cells which consequently causes "prometaphase arrest"; thus, inhibiting the cell growth and cell division and ultimately leading to death of the breast cancer cell. Similar results were found for 2-Methoxyestradiol that inhibited cancer cell growth by stimulating G2/M cell cycle arrest in MCF-7 cell line as well as MDA-MB-435 s cell lines, consequently enhancing apoptotic pathways due to its possible interaction with cytoskeleton protein fibers particularly with microtubules (Lin et al., 2000; Qadan et al., 2001; Kumar et al., 2001 Ray et al., 2006; Fukui and Zhu, 2009; Stander et al., 2010; Choi and Zhu, 2012).

Apoptotic cell death may be caused as a result of binding of microtubule inhibitors with tubulins or microtubules followed with suppression of microtubule dynamics and activities. This stimulates G2/M cell cycle arrest and ultimately causes apoptotic cell death (Wendell et al., 1993; Vasquez et al., 1997; Jordan and Wilson, 1998; Wang et al., 1999; Ghosh et al., 2003; Mollinedo and Gajate, 2003; Choi and Zhu, 2012). A study conducted by Wesierska-G et al. (2004) also depicted the same mode of action; he discovered that the G/M cell cycle arrest caused by roscovitine (CDK inhibitor) inhibited the cell division in MCF-7 cells while S/G phase transient was prevented by olomoucine (another CDK inhibitor).

This current study took 3 different chicken cathelicidin peptides with the intention to evaluate their efficacy in the treatment of breast cancer cells by stimulation of pro-apoptotic pathway and augmentation of the anti-proliferative activity. The study showed two- and three-times higher expression of the caspase-3, and -7 genes respectively in MCF-7 cells treated with chicken peptides (especially cathelicidin-2 and -3) relative to untreated cells.

The caspase-3 and -7 are executioner proteases. These findings corresponded to the findings of various other research works that suggested the stimulating effect of 20-40 µM of human cathelicidins on caspase proteases pathways and elicited autophagy and apoptosis in case of colon cancer as indicated by (Kuroda et al., 2012; Yang et al., 2003; Ren et al., 2013). The testing of most of the human breast tumors revealed deficiency of caspase-3 gene expression. Even the apparently normal breast parenchyma of patients with breast cancer showed loss of expression of caspase-3 gene. Caspase-3 belongs to cysteine protease family which is recognized for its contribution in apoptosis execution. Moreover, it was discovered that chemotherapeutic agents, irradiation, and cytokines as well as other apoptotic stimuli can activate caspase-3 (Salvesen and Dixit, 1997).

On the other hand, cell death was inhibited as a result of selective inhibition of caspase-3 gene (Hasegawa et al., 1996; Silke et al., 2001). Hence, it may be concluded that breast cancer cells are likely to become resistant to the interventions like radiation therapy and chemotherapy due to lower expression of caspase-3 gene. This explains the insensitivity of the MCF-7 cells with low expression of caspase-3 gene to cisplatin, doxorubicin and etoposide; this low expression may be attributed to functional deletion mutation in the caspase-3 gene. But the sensitivity to the mentioned medications and apoptotic stimuli can be restored by reconstituting the MCF-7 cells with caspase-3 gene (Yang et al., 2001).

On the contrary, morphological apoptosis was seen in MCF-7 cells as they respond to various agents even in the absence of caspase-3 expression (Eck-Enriquez et al., 2000). This indicates that these agents have the property to stimulate caspase-independent cell death (as through AIF; Cande et al., 2002) or caspase-dependent apoptosis through alternative downstream caspases, including caspase-6 and -7 (Liang et al., 2001).

The outcomes of our study indicated that before the treatment of MCF7 cells with peptides, the membranes of these cells were not disrupted; however, when the breast cancer cells were subjected to chicken peptide of 50 µg/ml concentration, the cell membranes were found to be disrupted which is evident from comparatively higher stain permeability than the untreated cells and extreme alteration and depolarization in cell morphology of the treated cells. Moreover, the shape of the mitochondria in treated cells is also elongated due to the effect of peptides on mitochondrial membrane. The nucleus of the treated cells undergoes fragmentation and is also smaller in size than in untreated cells.

The classical way of cancer's treatment from chemo- and radio-therapies to surgical interference have significantly evolved which brings a great step to reduce the morbidity and mortality caused by cancers. But it does not prevent inconvenience or undesirable effects. Nonetheless, new therapies have rapidly appeared such as immunotherapy which is classified as crucial alternative in various cases (Arruebo et al., 2011). Further, this therapy could impressively adapt with new faced challenges via enhancing new antitumor molecules which reinforce the body's immune functions. A large spectrum of immunotherapies against cancer proved efficient in several patients via checkpoint blockers, monoclonal antibodies, vaccines, and immune cell-based therapies (Ventola, 2017).

Recently, new studies are focused on finding more accurate approaches to further develop the therapeutic strategies for cancers. Once recently used tool is antimicrobial peptides (AMPs) which partially belong to the innate immune system in several species.

Cathelicidin peptides possess a large spectrum of functionality, including a direct antibiotic effects against fungus, bacteria, parasites, viruses and microorganisms. Thus, they can deeply modulate the immune or inflammatory reaction. Further, they demonstrated a chemotactic function in neutrophils, monocytes, and T lymphatic cells by stimulating the damaged vascular or in re-epithelization of injured skin. Further, they are implicated in beating cancer as antitumor factors (De Smet & Contreras, 2005) and they possess the ability to interact with different effector of immune cells. These cells include monocytes, macrophages, dendritic cells, lymphocytes, epithelial cells, and neutrophils. Many of these functions are still not fully defined, but a range of different receptors are involved. These receptors include FPR2 (also known as FPRL-1), CXCR2, and P2X7R (Barlow et al. 2014). The helical cathelicidin peptides have received much attention as a potential therapeutic agent. Herein, the objective was to investigate the role of chicken cathelicidin in Ehrlich ascites cell (EAC) suppression as a tumor model after subcutaneous implantation in mice. In addition, through this research work evaluated the therapeutic effect of chicken cathelicidin on the innate and adaptive antitumor immunity.

The INF-γ and TNFα populations were measured in the serum of all study animals using flow cytometric technique. Notwithstanding, Interferon-γ (INF-γ) is ranged as pleiotropic cytokine which is principally expressed via cytotoxic T lymphatic cells and natural killer (NK) cells. It could activate several pathways to inhibit the tumor growth (Ni & Lu, 2018). Tumor necrosis factor alpha (TNFα) which has a role in a variety of signaling events inside the cells and has demonstrated that during acute inflammation, macrophage and monocytes produce the inflammatory cytokines. TNFα is important for infection resistance and cancer and it exerts many of its action effects by binding to TNF receptor (TNFR) and this mechanism will cause necrosis or apoptosis (Idriss and Naismith 2000).

Our data showed that chicken cathelicidin (CATH-1) enhanced release of TNFα and INF-γ in treated mice groups. This observation could be attributed to the effect of cathelicidin in stimulating of the innate immune system cells to release INF-γ and TNFα which eradicate cancer cells.

We assessed the effect of cathelicidin in the expression of granzymes as determined by RT-qPCR. Chicken cathelicidin-1 increased expression of granzyme K involved in the induction of apoptosis. This partly explained that cathelicidin induces cytotoxic T cells and natural killer (NK) cells to release the pore-forming perforin together with a variety of granule-associated proteases including granzymes that mediate apoptosis via a cleavage of caspase-3 which results in DNA fragmentation (Bots and Medema 2006) and this finding is in line with previous study that demonstrated that cathelicidin induced leakage of granzymes from cytolytic granules in CD57BL/6 lymphocytes of mice treated with LL-37 (Mader et al. 2011). In parallel, the tumor size in untreated EAC-bearing group was significantly larger and elevated. However, the volume of this tumor was reduced in the treated EAC-bearing groups with chicken cathelicidin. Additionally, animals receiving a high dose of cathelicidin-1 (40 μg/ml) displayed an apical survival rate compared to untreated carcinoma control and animals which received a low dose of cathelicidin (10 and 20 μg/ml).

These results were supported by the histopathological examination of cancer tissues. Tumors of groups treated with chicken cathelicidin displayed high areas of necrosis. In contrast, cancer sections of untreated EAC-bearing mice showed high-grade malignant growth with minimal necrotic areas, and features of cancer cell proliferation. Moreover, the histological examination and immunohistochemical staining with Bcl2 marker revealed that the tumor section in Ehrlich solid tumor in untreated control exhibited a strong positive reaction for Bcl2 expression. In contrast, mild to moderate positive reactions for Bcl2 expression were detected in mice treated with 10 and 20 μg/ml of cathelicidin. Interestingly, few positive reactions for Bcl2 between extensive negative cells were observed in mice administered 40 μg/ml of cathelicidin. Similar findings were observed in a study showed apoptogenic effect of cathelicidin in colon cancer cells (HCT116) and Jurkat human T leukemia cells via upregulation of Bax and Bak and downregulation of Bcl2 which confirmed by TUNEL assay and Annexin V/PI staining (Ren et al. 2012, Mader et al. 2009).

In the current study, solid tumors grown in mice treated with a high dose of the Cathelicidin (40 μg/ml) exhibited significant increase of the necrosis area percentage and significant decrease of the BCL-2 immunostaining with significant decrease of the total histological scoring of the tumor mass. These results support the idea that the high dose of the chicken cathelicidin-1 has antitumor effect against solid tumors in mice. Our results provided further evidence of the potential role of cathelicidin as anti-cancer therapy and clearly increased apoptosis levels in EAC-bearing mice bearing. Our findings are in line with previous studies that demonstrate that LL-37 can apply the anti-cancer effects and mediate apoptosis in several types of cancer including gastric cancer, hematologic malignancy, and colon cancer (Piktel et al. 2016, Wu, Wang, et al. 2010, Wu, Sung, et al. 2010, An et al. 2005).

The different experiments in this study demonstrated that variations in the cytotoxic nature of LL-37 may potentially relate to peptide-mediated augmentation of innate immunity. These in vivo results showed that chicken cathelicidin exerted anti-proliferative and anti-cancer cytotoxicity against cancer cells. The anti-tumor cytotoxicity of chicken cathelicidin was correlated with an upgraded survival of EAC-bearing mice, reducing the tumor size and inducing apoptosis of cancer cells. According to our observation, we can state that chicken cathelicidin induced cytotoxic antitumor and anti-proliferative effects against cancer cells in EAC-bearing mice by enhancing antitumor immunity.

CONCLUSION

Our study concluded that cancer cell line growth was significantly inhibited (around 85-95%) when treated with high concentration of chicken cathelicidins (40 μg/ml) at 72 h of treatment which proves to be a strong anti-cancer agent. It was found that the untreated MCF-7 cell show expression of both the cyclin A1 and cyclin D while cells treated with chicken cathelicidins peptides do not depict clear expression of these genes. The cells treated in this way may sometimes even depict cell cycle division arrest in the cell cycle phases of G1/S and G2/S (prometaphase arrest) consequently inhibiting the growth of breast cancer cell line and ultimately causing death of cancer cell. Our finding shows that cathelicidin-1 induced a detectable level of caspase-3 gene expression which was 3 times greater than the expression of this gene in untreated cells whereas, treatment with cathelicidin-2 and -3 induced two times greater gene expression. The treatment with cathelicidin-2 and -3 resulted in two-fold caspase-7 gene expression than the expression of this gene in untreated MCF-7 cells. However, treatment of cancer cells with cathelicidin-1 did not show any change in caspase-7 gene expression. Our data showed that chicken (CATH-1) enhanced release of TNFα, INF-γ and upregulation of granzyme K in treated mice groups, in parallel, the tumor size and volume was reduced in the treated EAC-bearing groups after cathelicidin administration compared to untreated EAC-bearing group. Additionally, animals receiving a high dose of cathelicidin-1 (40 μg/ml) displayed an apical survival rate compared to untreated carcinoma control and animals which received a low dose of cathelicidin (10 and 20 μg/ml). Tumor of mice groups treated with chicken cathelicidin displayed a high area of necrosis compared to untreated EAC-bearing mice.

Histological analysis and immunohistochemical staining revealed that the tumor section in Ehrlich solid tumor exhibited a strong Bcl2 expression in untreated control compared to mice treated with 10 and 20 μg/ml of cathelicidin. Interestingly, low expression of Bcl2 was observed in mice administered 40 μg/ml of CATH-1. The outcomes of our study indicate that administration of chicken cathelicidin peptides reduces the tumor growth and induces necrosis of cancer cells in vivo via releasing TNFα and granule enzymes which mediate apoptosis pathways.

Acknowledgements

The inventors thank King Abdulaziz City for Science and Technology for technical and financial support under grant no. (14-Bio883-03). In addition, the inventors thank King Abdulaziz University, Science and technology unit (STU) for technical and financial support where the research was achieved at its laboratories.

REFERENCES

Achanta, M.; Sunkara, L. T.; Dai, G.; Bommineni, Y. R.; Jiang, W.; Zhang, G. Tissue expression and developmental regulation of chicken cathelicidin antimicrobial peptides. J. Anim Sci. Biotechnol. 2012, 3, 15

Al-Benna S, Shai Y, Jacobsen F, Steinstraesser L. Oncolytic activities of host defense peptides. Int J Mol Sci (2011) 12(11):8027-51. doi:10.3390/ijms12118027

Blagoskonny M V, Pardee A B: Exploiting cancer cell cycling for selective protection of normal cells. Cancer Res, 2001, 61, 4301-4305

Breen E C, Walsh J J. Tubulin-targeting agents in hybrid drugs. Curr Med Chem (2010) 17(7):609-39. doi:10.2174/092986710790416254

Chen Y, Mant C T, Farmer S W, Hancock R E, Vasil M L, Hodges R S. Rational design of alpha-helical antimicrobial peptides with enhanced activities and specificity/therapeutic index. J Biol Chem (2005) 280(13):12316-29. doi:10.1074/jbc.M413406200

Chen, X., Zoua, X., Qi, G., Tanga, Y., Guo, Y., Si, J., Liang, L. Roles and Mechanisms of Human Cathelicidin LL-37 in Cancer. Cell Physiol Biochem 2018; 47:1060-1073

Chuang C M, Monie A, Wu A, Mao C P, Hung C F. Treatment with LL-37 peptide enhances antitumor effects induced by CpG oligodeoxynucleotides against ovarian cancer. Hum Gene Ther (2009) 20(4):303-13. doi: 10.1089/hum.2008.124

Ciruelos Gil E M. Targeting the PI3K/AKT/mTOR pathway in estrogen receptor-positive breast cancer. Cancer Treat Rev (2014) 40(7):862-71. doi:10.1016/j. ctrv.2014.03.004

Coorens M, van Dijk A, Bikker F, Veldhuizen Haagsman H P (2015) Importance of endosomal cathelicidin degradation to enhance DNA-induced chicken macrophage activation. J Immunol 195(8); 3970-3977

Coorens M, Schneider V A, de Groot A M, van Dijk A, Meijerink M, Wells J M, Scheenstra M R, Veldhuizen E J, Haagsman H P (2017) Cathelicidins inhibit *Escherichia coli*—induced tlr2 and tlr4 activation in a viability-dependent manner. J Immunol 199(4):1418-1_428

Cuperus, T.; Coorens, M.; van Dijk, A.; Haagsman, H. P. Avian host defense peptides. Dev. Comp. Immunol. 2013, 41, 352-369

Cuperus T, van Dijk A, Matthijs M G, Veldhuizen E J, Haagsman H P (2016) Protective effect of in ovo treatment with the chicken cathelicidin analog D-CATH-2 against avian pathogenic *E. coli*. Sci Rep 6:26622

Dennison S R, Harris F, Bhatt T, Singh J, Phoenix D A. A theoretical analysis of secondary structural characteristics of anticancer peptides. Mol Cell Biochem (2010) 333(1-2):129-35. doi:10.1007/s11010-009-0213-3

Dennison S R, Whittaker M, Harris F, Phoenix D A. Anticancer alpha-helical peptides and structure/function relationships underpinning their interactions with tumour cell membranes. Curr Protein Pept Sci (2006) 7(6):487-99. doi:10.2174/138920306779025611

Fukui, M., B. T. Zhu, Mechanism of 2-methoxyestradiol-induced apoptosis and growth arrest in human breast cancer cells, Mol. Carcinog. 48 (2009) 66-78.

Ghosh, R., A. M. Ott, D. Seetharam, T. J. Slaga, A. P. Kumar, Cell cycle block and apoptosis induction in a human melanoma cell line following treatment with 2-methoxyoestradiol: therapeutic implications? Melanoma Res. 13 (2003) 119-127.

Goitsuka, R.; Chen, C. L.; Benyon, L.; Asano, Y.; Kitamura, D.; Cooper, M. D. Chicken cathelicidin-B1, an antimicrobial guardian at the mucosal M cell gateway. Proc. Natl. Acad. Sci. USA 2007, 104, 15063-15068.

Harris F, Dennison S R, Singh J, Phoenix D A. On the selectivity and efficacy of defense peptides with respect to cancer cells. Med Res Rev (2013) 33(1):190-234. doi: 10.1002/med.20252

Hase K, Murakami M, Iimura M, Cole S P, Horibe Y, Ohtake T, et al. Expression of LL-37 by human gastric epithelial cells as a potential host defense mechanism against *Helicobacter pylori*. Gastroenterology (2003) 125(6):1613-25. doi:10.1053/j.gastro.2003.08.028

Higgins G S, O'Cathail S M, Muschel R J, McKenna W G. Drug radiotherapy combinations: review of previous failures and reasons for future optimism. Cancer Treat Rev (2015) 41(2):105-13. doi:10.1016/j.ctrv.2014.12.012

Huang Y B, Wang X F, Wang H Y, Liu Y, Chen Y. Studies on mechanism of action of anticancer peptides by modulation of hydrophobicity within a defined structural framework. Mol Cancer Ther (2011) 10(3):416-26. doi: 10.1158/1535-7163. MCT-10-0811

Iwasaki T, Ishibashi J, Tanaka H, Sato M, Asaoka A, Taylor D, Yamakawa M. 2009. Selective cancer cell cytotoxicity of enantiomeric 9-mer peptides derived from beetle defensins depends on negatively charged phosphatidylserine on the cell surface. Peptides 30:660-668.

Johansson J, Gudmundsson G H, Rottenberg M E, Berndt K D, Agerberth B. Conformation-dependent antibacterial activity of the naturally occurring human peptide LL-37. J Biol Chem (1998) 273(6):3718-24. doi:10.1074/jbc.273.6.3718

Jordan, M. A., L. Wilson, Microtubules and actin filaments: dynamic targets for cancer chemotherapy, Curr. Opin. Cell Biol. 10 (1998) 123-130.

Karczmarek-Borowska B, Salek-Zan A. Hepatotoxicity of molecular targeted therapy. Contemp Oncol (Pozn) (2015) 19(2):87-92. doi:10.5114/wo.2014.43495 44. Ruan K, Song G, Ouyang G. Role of hypoxia in the hallmarks of human cancer. J Cell Biochem (2009) 107 (6):1053-62. doi:10.1002/jcb.22214

Kumar, A. P., G. E. Garcia, T. J. Slaga, 2-methoxyestradiol blocks cell-cycle progression at G2/M phase and inhibits growth of human prostate cancer cells, Mol. Carcinog. 31 (2001) 111-124.

Kuroda K, Fukuda T, Isogai H, Okumura K, Krstic-Demonacos M, Isogai E. Antimicrobial peptide FF/CAP18 induces apoptotic cell death in HCT116 colon cancer cells via changes in the metabolic profile. Int J Oncol (2015) 46(4):1516-26. doi:10.3892/ijo.2015.2887

Kuroda K, Fukuda T, Yoneyama H, Katayama M, Isogai H, Okumura K, et al. Anti-proliferative effect of an analogue of the LL-37 peptide in the colon cancer derived cell line HCT116 p53+/+ and p53. Oncol Rep (2012) 28(3):829-34. doi:10.3892/or.2012.1876

Kuroda K, Okumura K, Isogai H and Isogai E (2015) The human cathelicidin antimicrobial peptide LL-37 and mimics are potential anticancer drugs. Front. Oncol. 5:144. doi: 10.3389/fonc.2015.00144

Lee, M. O.; Jang, H. J.; Rengaraj, D.; Yang, S. Y.; Han, J. Y.; Lamont, S. J.; Womack, J. E. Tissue expression and antibacterial activity of host defense peptides in chicken. BMC Vet. Res. 2016, 12, 231

Lee, M. O.; Kim, E. H.; Jang, H. J.; Park, M. N.; Woo, H. J.; Han, J. Y.; Womack, J. E. Effects of a single nucleotide polymorphism in the chicken NK-lysin gene on antimicrobial activity and cytotoxicity of cancer cells. Proc. Natl. Acad. Sci. USA 2012, 109, 12087-12092.

Li Y, Cozzi P J. Angiogenesis as a strategic target for prostate cancer therapy. Med Res Rev (2010) 30(1):23-66. doi:10.1002/med.20161

Li Y C, Park M J, Ye S K, Kim C W, Kim Y N. Elevated levels of cholesterol-rich lipid rafts in cancer cells are correlated with apoptosis sensitivity induced by cholesterol-depleting agents. Am J Pathol (2006) 168(4):1107-18. doi:10.2353/ajpath.2006.050959

Lin, H. L., T. Y. Liu, G. Y. Chau, W. Y. Lui, C. W. Chi, Comparison of 2-methoxyestradiolinduced, docetaxel-induced, and paclitaxel-induced apoptosis in hepatoma cells and its correlation with reactive oxygen species, Cancer 89 (2000) 983-994.

Livak, K. J and Schmittgen, T. D. Analysis of relative gene expression data using real-time quantitative PCR and the 2(−Delta Delta C(T)) method. Methods 25: 402-408, 2001.

Liu F S. Mechanisms of chemotherapeutic drug resistance in cancer therapy—a quick review. Taiwan J Obstet Gynecol (2009) 48(3):239-44. doi:10.1016/S1028-4559(09) 60296-5

Lorin A, Noel M, Provencher M E, Turcotte V, Masson C, Cardinal S, et al. Revisiting peptide amphiphilicity for membrane pore formation. Biochemistry (2011) 50(43): 9409-20. doi:10.1021/bi201335t Mader J S, Mookherjee N, Hancock R E, Bleackley R C. The human host defense peptide LL-37 induces apoptosis in a calpain- and apoptosis-inducing factordependent manner involving Bax activity. Mol Cancer Res (2009) 7(5):689-702. doi:10.1158/1541-7786.MCR-08-0274

Matsuzaki K, Sugishita K, Fujii N, Miyajima K. Molecular basis for membrane selectivity of an antimicrobial peptide, magainin 2 Biochemistry (1995) 34(10):3423-9. doi:10.1021/bi00010a034

Mollinedo, F., C. Gajate, Microtubules, microtubule-interfering agents and apoptosis, Apoptosis 8 (2003) 413-450.

Nurse P: Cyclin dependent kinases and cell cycle control (Nobel lecture). Chembiochem, 2002, 3, 596-603.

Oren Z, Lerman J C, Gudmundsson G H, Agerberth B, Shai Y. Structure and organization of the human antimicrobial peptide LL-37 in phospholipid membranes: relevance to the molecular basis for its non-cell-selective activity. Biochem J (1999) 341(Pt 3):501-13. doi:10.1042/0264-6021:3410501

Ozben T. Mechanisms and strategies to overcome multiple drug resistance in cancer. FEBS Lett (2006) 580(12): 2903-9. doi:10.1016/j.febslet.2006.02.020 46. Goda K, Bacso Z, Szabo G. Multidrug resistance through the spectacle of P-glycoprotein. Curr Cancer Drug Targets (2009) 9(3):281-97. doi:10.2174/156800909788166493

Parvy, J. P., Yu, Y., Dostalova, A., Kondo, S., Kurjan, A., Bulet, P., Lemaitre, B., Vidal, M., Cordero, J. M. The antimicrobial peptide defensin cooperates with tumour necrosis factor to drive tumour cell death in *Drosophila*. eLife 2019; 8:e45061

Pathania D, Millard M, Neamati N. Opportunities in discovery and delivery of anticancer drugs targeting mitochondria and cancer cell metabolism. Adv Drug Deliv Rev (2009) 61(14):1250-75. doi:10.1016/j.addr.2009.05.0105

Peng L, Du W, Balhuizen M D, Haagsman H P, de Haan C A M, Veldhuizen D A (2020a) Antiviral activity of chicken cathelicidin B1 against influenza A virus. Front Microbiol 11:426

Peng L, Du W, Balhuizen M D, Haagsman H P, de Haan C A M, Veldhuizen E J A (2020b) The immunomodulatory effect of cathelicidin-B1 on chicken macrophages. Veterinary Research volume 51, 122

Qadan, L. R., C. M. Perez-Stable, C. Anderson, G. D'Ippolito, A. Herron, G. A. Howard, B. A. Roos, B A, 2-Methoxyestradiol induces G2/M arrest and apoptosis in prostate cancer, Biochem. Biophys. Res. Commun. 285 (2001) 1259-1266.

Ray, G. G. Dhar, P. J. Van Veldhuizen, S. Banerjee, N. K. Saxena, K. Sengupta, S. K. Banerjee, Modulation of cell-cycle regulatory signaling network by 2-methoxyestradiol in prostate cancer cells is mediated through multiple signal transduction pathways, Biochemistry 45 (2006) 3703-3713.

Ren S X, Shen J, Cheng A S, Lu L, Chan R L, Li Z J, et al. FK-16 derived from the anticancer peptide LL-37 induces caspase-independent apoptosis and autophagic cell death in colon cancer cells. PLoS One (2013) 8(5):e63641. doi:10.1371/journal.pone.0063641

Riedl S, Zweytick D, Lohner K. Membrane-active host defense peptides—challenges and perspectives for the development of novel anticancer drugs. Chem Phys Lipids (2011) 164(8):766-81. doi:10.1016/j.chemphyslip.2011.09.004

Simons K, Ikonen E. How cells handle cholesterol. Science (2000) 290(5497):1721-6. doi:10.1126/science.290.5497.1721

Stander, B. A., S. Marais, C. J. Vorster, A. M. Joubert, In vitro effects of 2-methoxyestradiol on morphology, cell cycle progression, cell death and gene expression changes in the tumorigenic MCF-7 breast epithelial cell line, J. Steroid Biochem. Mol. Biol. 119 (2010) 149-160.

Steiner H, Andreu D, Merrifield R B. Binding and action of cecropin and cecropin analogues: antibacterial peptides from insects. Biochim Biophys Acta (1988) 939(2):260-6. doi:10.1016/0005-2736(88)90069-7

Thomas H, Coley H M. Overcoming multidrug resistance in cancer: an update on the clinical strategy of inhibiting p-glycoprotein. Cancer Control (2003) 10(2):159-65.

Urruticoechea A, Alemany R, Balart J, Villanueva A, Vinals F, Capella G. Recent advances in cancer therapy: an overview. Curr Pharm Des (2010) 16(1):3-10. doi: 10.2174/138161210789941847

Vasquez, R. J., B. Howell, A. M. Yvon, P. Wadsworth, L. Cassimeris, Nanomolar concentrations of nocodazole alter microtubule dynamic instability in vivo and in vitro, Mol. Biol. Cell 8 (1997) 973-985.

Vincenzi B, Imperatori M, Silletta M, Marrucci E, Santini D, Tonini G. Emerging kinase inhibitors of the treatment of gastric cancer. Expert Opin Emerg Drugs (2015):1-15. doi:10.1517/14728214.2015.1051467

Van Dijk A, Tersteeg-Zijderveld M H, Tjeerdsma-van Bokhoven J L, Jansman A J, Veldhuizen E J, Haagsman H P (2009) Chicken heterophils are recruited to the site of *Salmonella* infection and release antibacterial mature Cathelicidin-2 upon stimulation with LPS. Mol Immunol 46(7):1517-1526

Van Dijk A, van Eldik M, Veldhuizen E J, Tjeerdsma-van Bokhoven H L, de Zoete M R, Bikker F J, Haagsman H P (2016) Immunomodulatory and anti-inflammatory activities of chicken cathelicidin-2 derived peptides. PLos One 11(2):e0147919

Wang G, Mishra B, Epand R F, Epand R M. High-quality 3D structures shine light on antibacterial, anti-biofilm and antiviral activities of human cathelicidin LL-37 and its fragments. Biochim Biophys Acta (2014) 1838(9):2160-72. doi:10.1016/j. bbamem.2014.01.016

Wang, T. H., D. M. Popp, H. S. Wang, M. Saitoh, J. G. Mural, D. C. Henley, H. Ichijo, J. Wimalasena, Microtubule dysfunction induced by paclitaxel initiates apoptosis through both c-Jun N-terminal kinase (JNK)-dependent and -independent pathways in ovarian cancer cells, J. Biol. Chem. 274 (1999) 8208-8216.

Wendell, K. L., L. Wilson, M. A. Jordan, Mitotic block in HeLa cells by vinblastine: ultrastructural changes in kinetochore-microtubule attachment and in centrosomes, J. Cell Sci. 104 (Pt 2) (1993) 261-274.

Wojcik C, Sawicki W, Marianowski P, Benchaib M, Czyba J C, Guerin J F. Cyclodextrin enhances spermicidal effects of magainin-2-amide. Contraception (2000) 62(2):99-103. doi:10.1016/S0010-7824(00)00143-8

Wu W K, Sung J J, To K F, Yu L, Li H T, Li Z J, et al. The host defense peptide LL-37 activates the tumor-suppressing bone morphogenetic protein signaling via inhibition of proteasome in gastric cancer cells. J Cell Physiol (2010) 223(1):178-86. doi:10.1002/jcp.22026

Wu W K, Wang G, Coffelt S B, Betancourt A M, Lee C W, Fan D, et al. Emerging roles of the host defense peptide LL-37 in human cancer and its potential therapeutic applications. Int J Cancer (2010) 127(8):1741-7. doi: 10.1002/ijc.25489

Xiao, Y; Cai, Y.; Bommineni, Y. R.; Fernando, S. C.; Prakash, O.; Gilliland, S. E.; Zhang, G. Identification and functional characterization of three chicken cathelicidins with potent antimicrobial activity. J. Biol. Chem. 2006, 281, 2858-2867

Yacoub H A, Ahmed M. Elazzazy, Maged M. Mahmoud, Mohamed Nabih Baeshen, Omar A. Al-Maghrabi, Saleh Alkarim, Ekram S. Ahmed, Hussein A. Almehdar, Vladimir N. Uversky (2016) Chicken cathelicidins as potent intrinsically disordered biocides with antimicrobial activity against infectious pathogens. Developmental and Comparative Immunology (65). 8-24.

Yang S T, Shin S Y, Lee C W, Kim Y C, Hahm K S, Kim J I. Selective cytotoxicity following Arg-to-Lys substitution in tritrpticin adopting a unique amphipathic turn structure. FEBS Lett (2003) 540(1-3):229-33. doi:10.1016/50014-5793(03)00266-7

Yang Y H, Zheng G G, Li G, Zhang B, Song Y H, Wu K F. Expression of LL-37/hCAP-18 gene in human leukemia cells. Leuk Res (2003) 27(10):947-50. doi:10.1016/50145-2126(03)00020-1 89. Ren S X, Cheng A S, To K F, Tong J H, Li M S, Shen J, et al. Host immune defense peptide LL-37 activates caspase-independent apoptosis and suppresses colon cancer. Cancer Res (2012) 72(24): 6512-23. doi:10.1158/0008-5472. CAN-12-2359

Zasloff, M. Antimicrobial Peptides of Multicellular Organisms: My Perspective. Adv. Exp. Med. Biol. 2019, 1117, 3-6.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

---

We claim:

1. A method of treating breast or colon cancer in a subject in need thereof, comprising administering to the subject a therapeutically effective amount of a chicken cathelicidin or an active analog thereof, wherein the active analog has at least 80% sequence identity to SEQ ID NO: 1, SEQ ID NO: 2, or SEQ ID NO: 3.

2. The method of claim 1, wherein the cathelicidin is cathelicidin-1.

3. The method of claim 1, wherein the cathelicidin is cathelicidin-2.

4. The method of claim 1, wherein the cathelicidin is cathelicidin-3.

5. The method of claim 1, wherein the chicken cathelicidin is administered at a dose of 5 to 45 mg/kg.

6. The method of claim 1, wherein the subject is human.

7. A method of inhibiting the growth of breast or colon cancer cells, comprising contacting the breast or colon cancer cells with an effective amount of a chicken cathelicidin or an active analog thereof, wherein the active analog has at least 80% sequence identity to SEQ ID NO: 1, SEQ ID NO: 2, or SEQ ID NO: 3.

8. The method of claim 7, wherein the cathelicidin is cathelicidin-1.

9. The method of claim 7, wherein the cathelicidin is cathelicidin-2.

10. The method of claim 7, wherein the cathelicidin is cathelicidin-3.

* * * * *